United States Patent
Graham et al.

(10) Patent No.: US 7,132,290 B2
(45) Date of Patent: *Nov. 7, 2006

(54) RECOMBINASE-BASED SYSTEM FOR COMBUSTION OF ADENOVIRUS VECTORS

(75) Inventors: Frank L. Graham, Hamilton (CA); Robin J. Parks, Ottawa (CA); Philip Ng, Caledonia (CA)

(73) Assignee: AdVec, Inc., Ancaster (CA)

( * ) Notice: Subject to any disclaimer, the term of this patent is extended or adjusted under 35 U.S.C. 154(b) by 18 days.

This patent is subject to a terminal disclaimer.

(21) Appl. No.: 09/909,414

(22) Filed: Jul. 19, 2001

(65) Prior Publication Data

US 2004/0142470 A1 Jul. 22, 2004

Related U.S. Application Data

(63) Continuation of application No. 09/263,650, filed on Mar. 5, 1999, now Pat. No. 6,379,943.

(51) Int. Cl.
*C12N 15/87* (2006.01)
*C12N 15/861* (2006.01)

(52) U.S. Cl. .................................. 435/462; 435/320.1

(58) Field of Classification Search ............. 435/235.1, 435/320.1, 325, 366
See application file for complete search history.

(56) References Cited

FOREIGN PATENT DOCUMENTS

WO    WO 97/25446    *   7/1997

OTHER PUBLICATIONS

Bett et al., An efficient and flexible system for construction of adenovius vectors with insertions or deletions in early regions 1 and 3, Sep. 1994, Proc. Natl. Acad. Sci. USA, vol. 91, pp. 8802-8806.*

* cited by examiner

*Primary Examiner*—Nancy Vogel
(74) *Attorney, Agent, or Firm*—Joseph Fischer; Beusse, Wolter, Sanks, Mora & Maire, PA

(57) ABSTRACT

In the present invention, viruses, plasmids or both are constructed which contain viral DNA and lox sites positioned such that site-specific recombination between lox sites in separate plasmids results in generation of infectious viral DNA at high-efficiency in cotransfected host cells that have been engineered to express the Cre recombinase. Because of the high-efficiency and specificity of the Cre enzyme, suitably engineered plasmids can be readily recombined to produce infectious virus at high-efficiency in cotransfected 293 cells, without, at the same time, producing wild-type adenovirus, with the attendant problems for removal thereof. Use of recombinases besides Cre and recombinase recognition sites besides lox sites, and use of cells other than 293 cells are also disclosed and enabled, as are kits incorporating the site-specific vector system.

21 Claims, 26 Drawing Sheets

Figure 3

OLIGONUCLEOTIDES USED IN CLONING

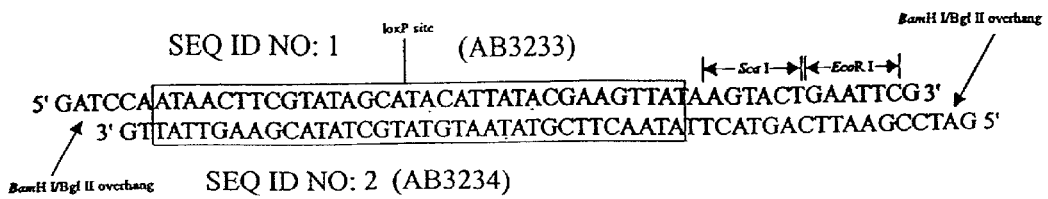

loxP linker Sequences

SEQ ID NO: 1 (AB3233)

5' GATCCAATAACTTCGTATAGCATACATTATACGAAGTTATAAGTACTGAATTCG 3'
3' GTTATTGAAGCATATCGTATGTAATATGCTTCAATATTCATGACTTAAGCCTAG 5'

SEQ ID NO: 2 (AB3234)

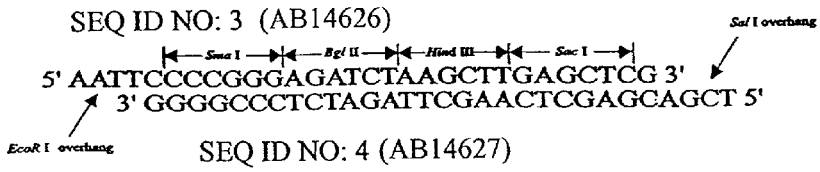

Multiple Cloning Site Sequences

SEQ ID NO: 3 (AB14626)

5' AATTCCCCGGGAGATCTAAGCTTGAGCTCG 3'
3' GGGGCCCTCTAGATTCGAACTCGAGCAGCT 5'

SEQ ID NO: 4 (AB14627)

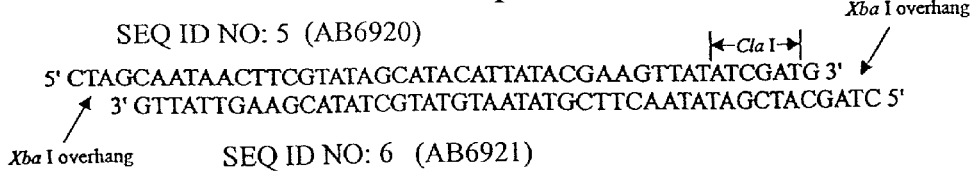

loxP linker Sequences

SEQ ID NO: 5 (AB6920)

5' CTAGCAATAACTTCGTATAGCATACATTATACGAAGTTATATCGATG 3'
3' GTTATTGAAGCATATCGTATGTAATATGCTTCAATATAGCTACGATC 5'

SEQ ID NO: 6 (AB6921)

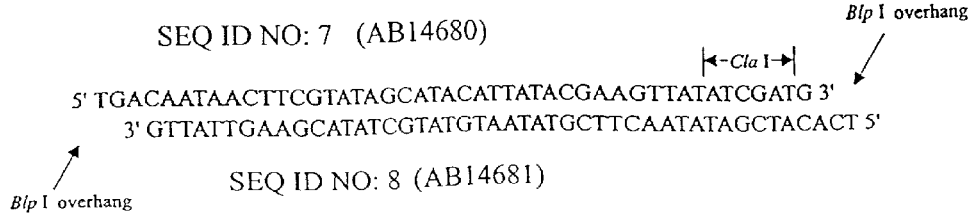

loxP linker Sequences

SEQ ID NO: 7 (AB14680)

5' TGACAATAACTTCGTATAGCATACATTATACGAAGTTATATCGATG 3'
3' GTTATTGAAGCATATCGTATGTAATATGCTTCAATATAGCTACACT 5'

SEQ ID NO: 8 (AB14681)

CONSTRUCTION OF A CIRCULAR GENOMIC PLASMID FOR Ad VECTOR RESCUE USING THE Cre/ loxP SYSTEM

CONSTRUCTION OF pBHGdX1Plox

CONSTRUCTION OF pBHGE3lox

CONSTRUCTION OF pMH4LOX, pMH4LOXΔ and pMH4LOXΔLINK SHUTTLE PLASMIDS FOR RESCUE OF EXPRESSION CASSETTES

CONSTRUCTION OF HCMV loxP PLASMIDS
FOR RESCUE OF EXPRESSION CASSETTES

CONSTRUCTION OF pCA36LOX and pCA36LOXΔ SHUTTLE PLASMIDS FOR RESCUE OF LACZ

Cotransfection of 293Cre cells with AdLC8c DNA-TP and a shuttle plasmid containing a loxP site for generation of Ad expression vectors

CONSTRUCTION OF pFG173lox
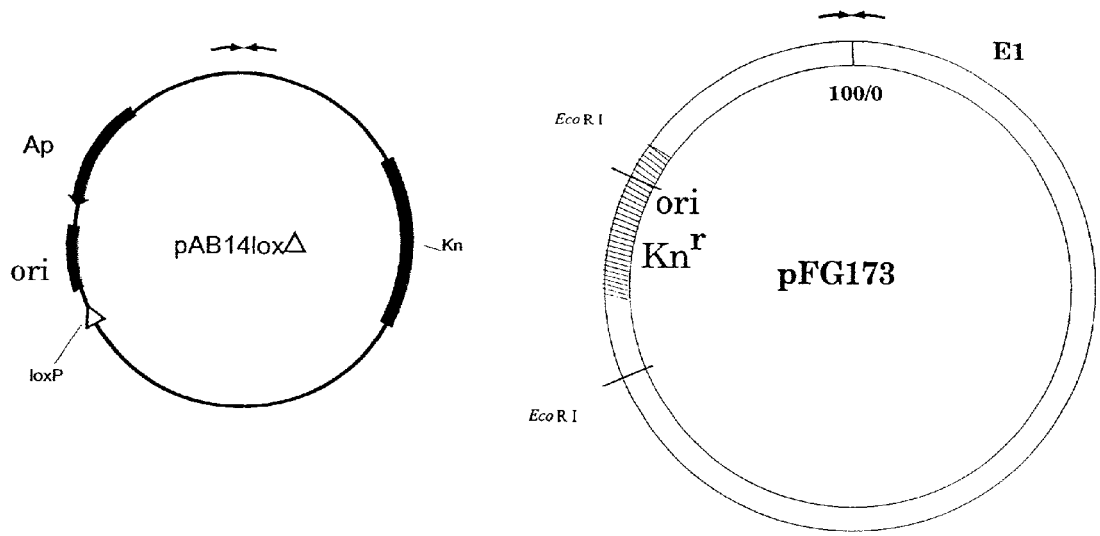
Restriction, transformation of E. coli, homologous recombination
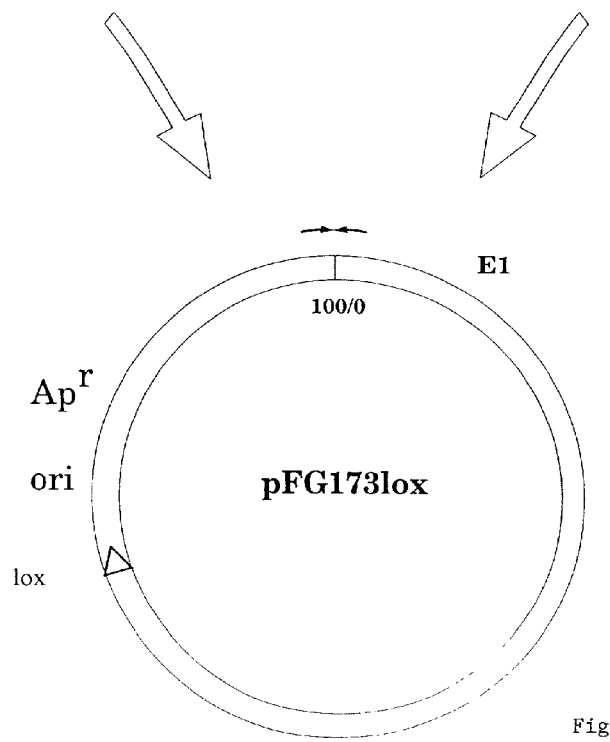
Figure 9C

CONSTRUCTION OF pAB14FL0X FOR ISOLATION OF AN AD VIRUS WITH A FLOXED FIBRE GENE

Isolation of a virus containing a fibre gene with flanking lox P sites.
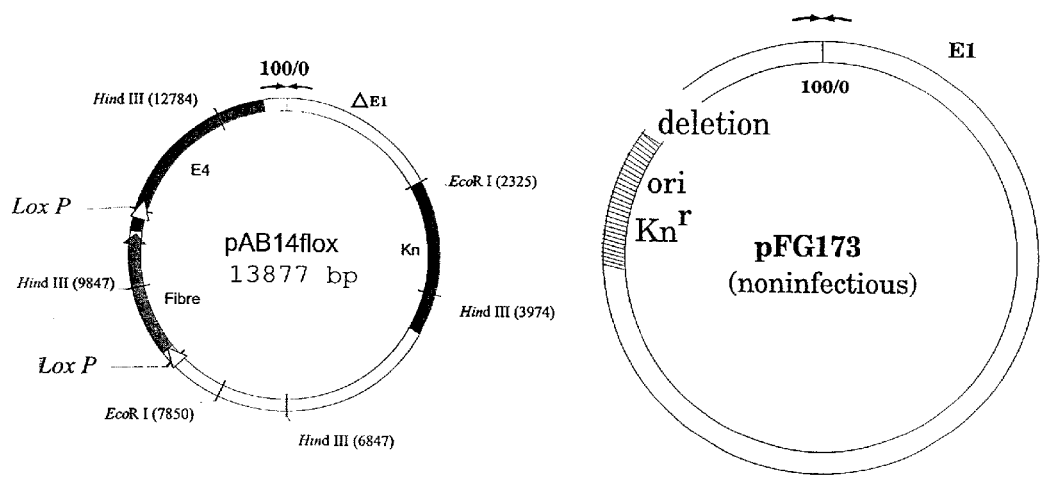
COTRANSFECTION OF 293 CELLS
HOMOLOGOUS RECOMBINATION
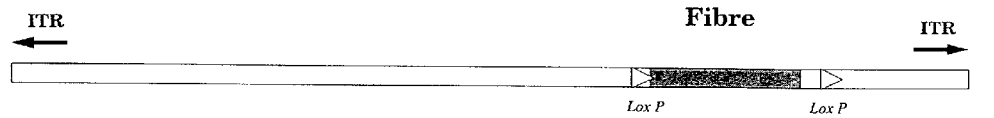
+
NONDEFECTIVE (E1⁻) VIRUS (ADFLOXFIBRE) CONTAINING A FLOXED FIBRE GENE
Figure 15

SEQUENCE LISTING

<160> NUMBER OF SEQ ID NOS: 9

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 1
gatccaataa cttcgtatag catacattat acgaagttat aagtactgaa ttcg            54

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 2
gatccgaatt cagtacttat aacttcgtat aatgtatgct atacgaagtt attg            54

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Linkers,
      primers, probes

```
<400> SEQUENCE: 3
aattccccgg gagatctaag cttgagctcg                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 4
tcgacgagct caagcttaga tctcccgggg                                    30

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 5
ctagcaataa cttcgtatag catacattat acgaagttat aatcgatg                48

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 6
ctagcatcga tataacttcg tataatgtat gctatacgaa gttattg                 47

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 7
tgacaataac ttcgtatagc atacattata cgaagttata tcgatg                  46

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Linkers,
      primers, probes

<400> SEQUENCE: 8
tcagatcgat ataacttcgt ataatgtatg ctatacgaag ttattg                  46

<210> SEQ ID NO 9
<211> LENGTH: 14
<212> TYPE: DNA
<213> ORGANISM: Artificial Sequence
<220> FEATURE:
```

```
-continued

<223> OTHER INFORMATION: Description of Artificial Sequence: Linkers,
      primers, probes

<400> SEQUENCE: 9
ctagcttaat taag                                                       14
```

RECOMBINASE-BASED SYSTEM FOR COMBUSTION OF ADENOVIRUS VECTORS

CROSS REFERENCE TO RELATED APPLICATION

This application is a continuation of parent application Ser. No. 09/263,650, filed on Mar. 5, 1999 now U.S. Pat. No. 6,379,943.

FIELD OF THE INVENTION

The present invention relates to methods for efficient and reliable construction of adenovirus vectors that contain and express foreign DNA and are useful for gene transfer into mammalian cells, for vaccines and for gene therapy. The vector system described herein is an improvement and modification of the pBHG system, described in U.S. Pat. No. 6,140,087 (Graham et al.), a foreign equivalent of which published as WO95/00655, both of which are hereby incorporated by reference.

BACKGROUND OF THE INVENTION

As taught in U.S. Pat. No. 6,140,087, adenoviruses (Ads) can be used as mammalian cell expression vectors, with excellent potential as live recombinant viral vaccines, as transducing vectors for gene therapy, for research, and for production of proteins in mammalian cells.

In the human Ad genome, early region 1 (E1), E3, and a site upstream of E4 have been utilized as sites for introducing foreign DNA sequences to generate adenovirus recombinants. In the absence of compensating deletions in E1 or E3, a maximum of about 2 kb can be inserted into the Ad genome to generate viable virus progeny. The E1 region is not required for viral replication in complementing 293 cells, or other cells known to complement E1, and up to 3.2 kb can be deleted in this region to generate conditional helper independent vectors with a capacity of 5.0–5.2 kb. In the E3 region, which is not required for viral replication in cultured cells, deletions of various sizes have been utilized to generate nonconditional helper independent vectors with a capacity of up to 4.5–4.7 kb. The combination of deletions in E1 and E3 permits the construction and propagation of adenovirus vectors with a capacity for insertions of up to approximately 8 kb of foreign DNA.

The construction of Adenovirus vectors can be performed in many ways. One approach is to cotransfect permissive cells, usually 293 cells, with a shuttle plasmid containing a portion of the left end of the Ad genome and, most commonly, having the E1 sequences replaced by a foreign DNA, and with DNA isolated from virions cleaved near the left end by a suitable restriction enzyme. Homologous recombination between overlapping viral DNA sequences of the shuttle plasmid and the virion DNA results in production of recombinant viruses containing the foreign DNA. A disadvantage of this method is the need to prepare purified viral DNA. In addition, such methods typically result in the presence of contaminating parental virus in the resulting vector preparations, such as when 100% of the viral DNA is not cleaved, or when the two viral DNA fragments produced by restriction cleavage are rejoined.

Another method has recently been described (Hardy S, Kitamura M, Harris-Stansil T, Dai Y, Phipps ML, "Construction of adenovirus vectors through Cre-lox recombination." J Virol 1997 March; 71(3):1842–1849; see also PCT publication WO97/32481 relating to use of site-specific recombination of virus and helper dependent vectors) which involves infection of 293Cre cells (293 cells engineered to express Cre recombinase) with an Adenovirus containing a floxed packaging signal ($\Psi$) and transfection with a shuttle plasmid containing an ITR, a packaging signal and an expression cassette followed by a lox site, or cotransfection of 293Cre cells with purified deproteinized Adenoviral DNA and a shuttle plasmid. According to that method, Cre-mediated excision of the packaging signal from virus followed by site-specific recombination with the lox site in the shuttle plasmid produces a recombinant vector containing the expression cassette. However, as Cre action is not 100% efficient, the resulting virus preparations remain contaminated with parental virus, and must be passaged in 293Cre cells to eliminate the contaminating parental virus. A further disadvantage of this method is that it requires use of an infectious virus or DNA extracted from a virus as one of the starting materials, and is thus less attractive for commercial distribution than kits containing only bacterial plasmid DNA. Furthermore, the parental virus can recombine with Ad E1 sequences present in 293 cells, resulting in a virus containing a wild-type packaging signal and a wild-type E1 region. Such recombinant virus has the propensity to overgrow the original vector, leading to contamination of subsequent vector preparations with non-attenuated E1 expressing Ads.

One of the most frequently used and most popular methods for construction of adenovirus vectors is based on "the two plasmid method" (see Bett et al., "Packaging capacity and stability of human adenovirus type 5 vectors," J. Virol. 67:5911–5921,1993), whereby suitable host cells (typically 293 cells) are cotransfected with two plasmids that separately are incapable of generating infectious virus, but which, when recombined within the transfected cell by homologous recombination, can generate replicating virus. The most widely used plasmids of this type are described in U.S. Pat. No. 6,140,087, hereby incorporated by reference. That system has advantages over other methods using viruses or viral DNA as components since only easily-prepared plasmid DNAs are needed, and there is no background of parental virus that could contaminate the final vector isolates. Furthermore, the plasmids are not only easy and inexpensive to produce by those skilled in the art, but can be easily stored and transported, making them convenient for commercial distribution, (i.e. particularly when precipitated with ethanol or when lyophilized, these vectors do not require a cold chain for distribution). However, although this currently available system has proven utility and is widely used, the efficiency of virus production by homologous recombination can be low and variable, and the system cannot always be used easily by those not skilled in the art.

As demonstrated in (Anton, M. and Graham, F. L. "Site-specific recombination mediated by an adenovirus vector expressing the Cre recombinase protein: a molecular switch for control of gene expression," J. Virol. 69:4600–4606, 1995), and as described also in parent application Ser. No. 08/486,549 ("Adenoviruses for control of gene expression", hereby incorporated by reference), provision of Cre recombinase in Ad-infected cells can catalyse excision or rearrangement of viral DNA sequences that contain the target sites (lox P) for Cre-mediated site-specific recombination. Such techniques are applied in new ways in the present invention disclosure to provide a long-needed advancement in the art of adenoviral vector production.

SUMMARY OF THE INVENTION

In the present invention, viruses, plasmids or both are constructed which contain viral DNA and lox P sites positioned such that site-specific recombination between lox P sites in separate plasmids results in generation of infectious viral DNA at high-efficiency in cotransfected host cells that have been engineered to express the Cre recombinase. Such cells (293Cre cells) have been described by Parks, R. J., Chen, L., Anton, M., Sankar, U., Rudnicki, M. A. and Graham, F. L. "A new helper-dependent adenovirus vector system: removal of helper virus by Cre-mediated excision of the viral packaging signal," Proc. Natl. Acad. Sci. U.S. 93: 13565–13570, 1996, by Chen, L., Anton, M. and Graham, F. L., "Production and characterization of human 293 cell lines expressing the site-specific recombinase Cre," Somat. Cell and Molec. Genet. 22: 477–488, 1996, in U.S. patent application Ser. No. 08/473,168, and in PCT publication WO96/40955, hereby incorporated by reference for this purpose. Because of the high-efficiency and specificity of the Cre enzyme, suitably engineered plasmids can be readily recombined to produce infectious virus at high-efficiency in cotransfected 293 cells, without, at the same time, producing a contaminating parental adenovirus, with the attendant problems for removal thereof.

In one embodiment, this invention provides a two plasmid system wherein homologous recombination via cellular enzymes is replaced by site specific recombination, via a recombinase such as Cre, to join (with high efficiency) two DNAs that separately are noninfectious to form an infectious DNA molecule. One application of the techniques disclosed herein is the isolation of "first generation" vectors with insertions of foreign DNA in E1. Such applications utilize a series of plasmids such as pBHG10lox (see FIG. 1, and variations and equivalents thereof), and various shuttle plasmids containing the left ITR, a packaging signal, an expression cassette, and a lox or other recombinase recognition site. Another application is in a sense the mirror image. Using a plasmid such as pFG173lox, sequences are rescued into the right end of the viral DNA, into E3 or into sites rightward of E3. The most important applications of this technology will likely be rescue of mutations into the fibre gene located immediately rightward of E3 (FIG. 9) (fibre is important because it is a major ligand for binding to cellular receptors) but one can also rescue mutations, deletions, insertions and other modifications in E4 genes (located between fibre and the right ITR) or use the method to rescue inserts of foreign DNA into E3 (cotransfection of a plasmid such as that depicted in FIG. 11 with pFG173lox). Note that the plasmid pFG173lox has a deletion of fibre, but E4 sequences could just as well be deleted as well as or instead of fibre. Note also that lox sites could be inserted at other locations in the Ad genome to enable the rescue of mutations engineered in other viral genes besides those of fibre or E4, or rescue of DNA inserts into other sites.

In a further embodiment of this invention, DNA-TP complexes are utilized to combine the high efficiency of Cre-lox recombination with the high infectivity of DNA-TP. While the rescue of infectious virus via Cre mediated recombination is surprisingly efficient compared to homologous recombination, and is more than adequate to produce viral vectors and to introduce mutations into the viral genome for most applications, there may be certain applications for which even higher efficiencies are desirable or necessary. It is known by those skilled in the art that the infectivity of adenovirus DNA is up to 100 fold higher if the virion DNA is extracted and purified by methods that leave intact the terminal protein (TP) that is normally linked to the 5' end of each strand of the duplex Ad DNA molecule (Sharp P A, Moore C, Haverty J L, "The infectivity of adenovirus 5 DNA-protein complex," Virology 1976 December; 75(2): 442–456, Chinnadurai G, Chinnadurai S, Green M, "Enhanced infectivity of adenovirus type 2 DNA and a DNA-protein complex." J Virol 1978 April; 26(1):195–199). For rescue of cassettes, the two plasmid system is more than sufficiently efficient, especially with the approximately 30-fold enhancement demonstrated herein for Cre-lox mediated recombination over homologous recombination, and consequently would be preferred for most purposes. However, there may be times when even higher efficiencies are required, as when, for example, one wishes to develop a library of fibre mutations (a large number of different viruses—the more the better). Then the chore of preparing DNA-TP might be worthwhile and could be accomplished by those skilled in the art. Thus, an aspect of the present invention includes the combination of the Cre-lox recombination with the high specific infectivity of adenoviral DNA-TP complexes.

Therefore, it is an object of the present invention to provide a highly efficient, reliable, and simple method for isolation of viral vectors based on site-specific recombination catalysed by a site-specific recombinase, such as but not limited to the Cre recombinase, rather than relying on homologous recombination, which depends on normal cellular recombinase pathways.

It is a further object of this invention to use Cre-lox-mediated recombination and known two plasmid vector production systems to provide a simple method for introducing mutations or other modifications of viral genes into any desired location in the viral genome.

It is a further object of this invention to provide a simple and useful system by which adenovirus cloning vectors may be developed.

It is a further object of this invention to provide a kit for production of adenoviral vectors for vaccine and gene-therapeutic applications which relies on site-specific recombination, rather than homologous recombination, and which does not require a cold-chain for distribution.

A further object of this invention is to provide a system whereby the high-efficiency of Cre-lox recombination is combined with enhanced infectivity achieved when adenovirus-TP complexes are utilized.

Further objects of this invention will become apparent from a review of the complete disclosure and the claims appended hereto.

BRIEF DESCRIPTION OF DRAWINGS

FIG. 3 illustrates four sets (pairs) of oligonucleotides used in various cloning procedures. The oligonucleotides are annealed prior to use to produce the double stranded DNA segments illustrated. Three of the oligonucleotide pairs contain loxP, the recognition site for Cre recombinase as well as one or more restriction endonuclease sites used for diagnostic purposes or for subsequent cloning steps. One of the oligonucleotide pairs contains several restriction endonuclease sites and was used to introduce a polycloning site into various shuttle plasmids.

FIGS. 4B-1 and 4B-2 illustrate the construction of a plasmid, pBHGdX1Plox, containing a modified E3 deletion (taken from pFG23dX1) and a lox site 5' of the pIX gene. The plasmid pFG23dX1P was constructed by inserting an oligonucleotide containing a PacI site (AB14566; 5'-CTAGCTTAATTAAG-3', SEQ ID NO:9; this oligo self anneals to produce a double stranded DNA with 5' overhangs that hybridize to overhangs generated by XbaI cleavage) into the XbaI site of pFG23dX1. The resulting plasmid, pFG23dX1P, is identical to pFG23dX1 except that the unique XbaI site at nt 11392 is changed to a unique Pac I site. The plasmid pNG17 was constructed by cloning the 6724 bp SpeI/ClaI fragment from pBHG10lox into pBluescript. The plasmid pNG17dX1P was constructed by replacing the 1354 bp SpeI/NdeI fragment from pNG17 with the 2143 bp SpeI/NdeI fragment from pFG23dX1P. Finally, the plasmid pBHGdX1Plox was constructed by replacing the 6724 bp SpeI/ClaI fragment from pBHG10lox with the 7513 bp SpeI/ClaI fragment from pNG17dX1P. pBHGdX1Plox thus contains a modified E3 region such that the deletion of E3 sequences is that of the parental plasmid pFG23dX1 (a deletion of 1878 bp) rather than the larger deletion of the other parental plasmid pBHG10lox.

FIG. 8c is also suitable for generation of an adenovirus vector.

FIG. 9C is a diagrammatic representation of a method for combining the plasmid of FIG. 9a with pFG173 to produce pFG173lox for rescuing fibre or E4 mutations into infectious virus using Cre-lox recombination. The plasmid pAB 14loxΔ is treated with restriction enzymes that cut in and around the kanamycin resistance gene and pFG173 is similarly digested with Eco RI as illustrated.

Transformation of *E. coli* with the fragmented DNA from the two plasmids results in formation of a replicating plasmid in which the sequences in and around the shaded portion indicated in pFG173 are substituted with corresponding sequences from pAB14loxΔ by homologous recombination (Chartier C, Degryse E, Gantzer M, Dieterle A, Pavirani A, Mehtali M. Efficient generation of recombinant adenovirus vectors by homologous recombination in *Escherichia coli*. J Virol 1996 July; 70(7):4805–4810).

Figure 10:
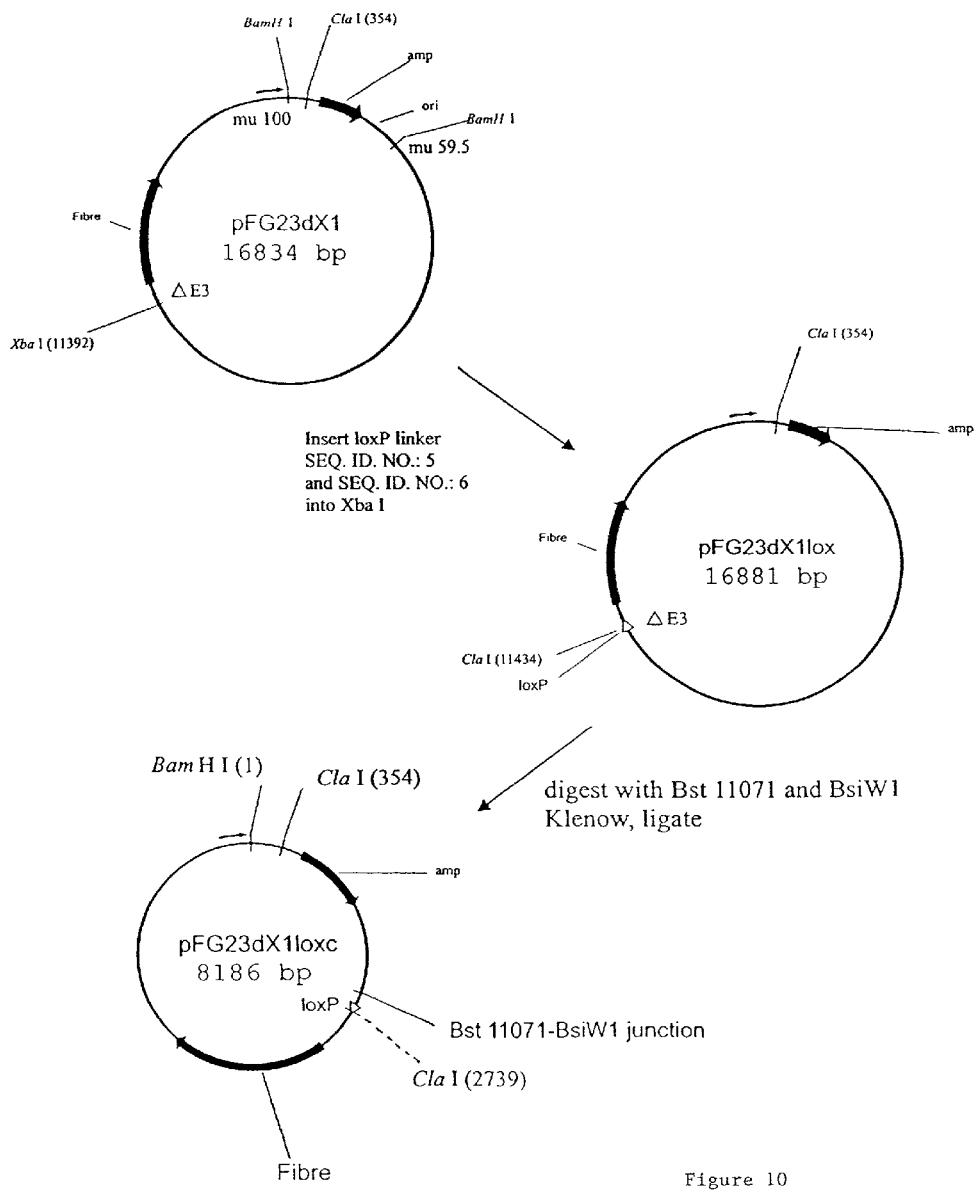

FIG. 10 is a diagrammatic representation of method for constructing a plasmid containing the right approximately 40% of the virus genome wherein a lox P site has been inserted near the 5' end of the fibre gene. The plasmid pFG23dX1 contains the right 40% of the Ad5 genome cloned into the bacterial plasmid pBR322, and has a deletion of an XbaI fragment from nt 28,589 (79.6 mu) of the wt Ad5 sequence to nt 30470 (mu 84.8) leaving a unique XbaI site suitable for insertion of a loxP site. A loxP site comprised of two synthetic oligonucleotides (SEQ ID NO:5 and SEQ ID NO:6; AB6920/AB6921, FIG. 3) was ligated into the XbaI site of pFG23dX1 to generate pFG23dX1lox which contains a loxP site upstream of the sequences encoding fibre. Finally, pFG23dX1lox was further modified by deletion of viral sequences between a unique Bst11071 site and a BsiW1 site immediately 5' of the lox P site to generate pFG23dX1loxc.

Figure 11:
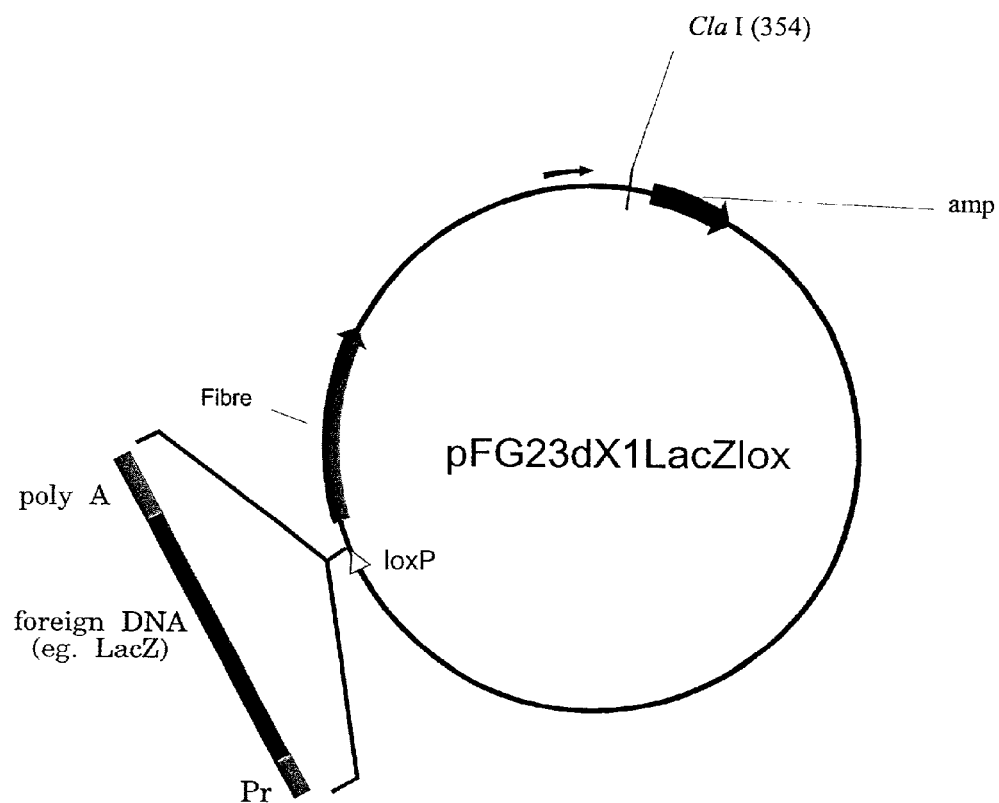

FIG. 11 illustrates a pFG23dX1lox plasmid with an expression cassette encoding bacterial β-galactosidase inserted into the Cla I site between the lox P site and the fibre gene.

Figure 12:
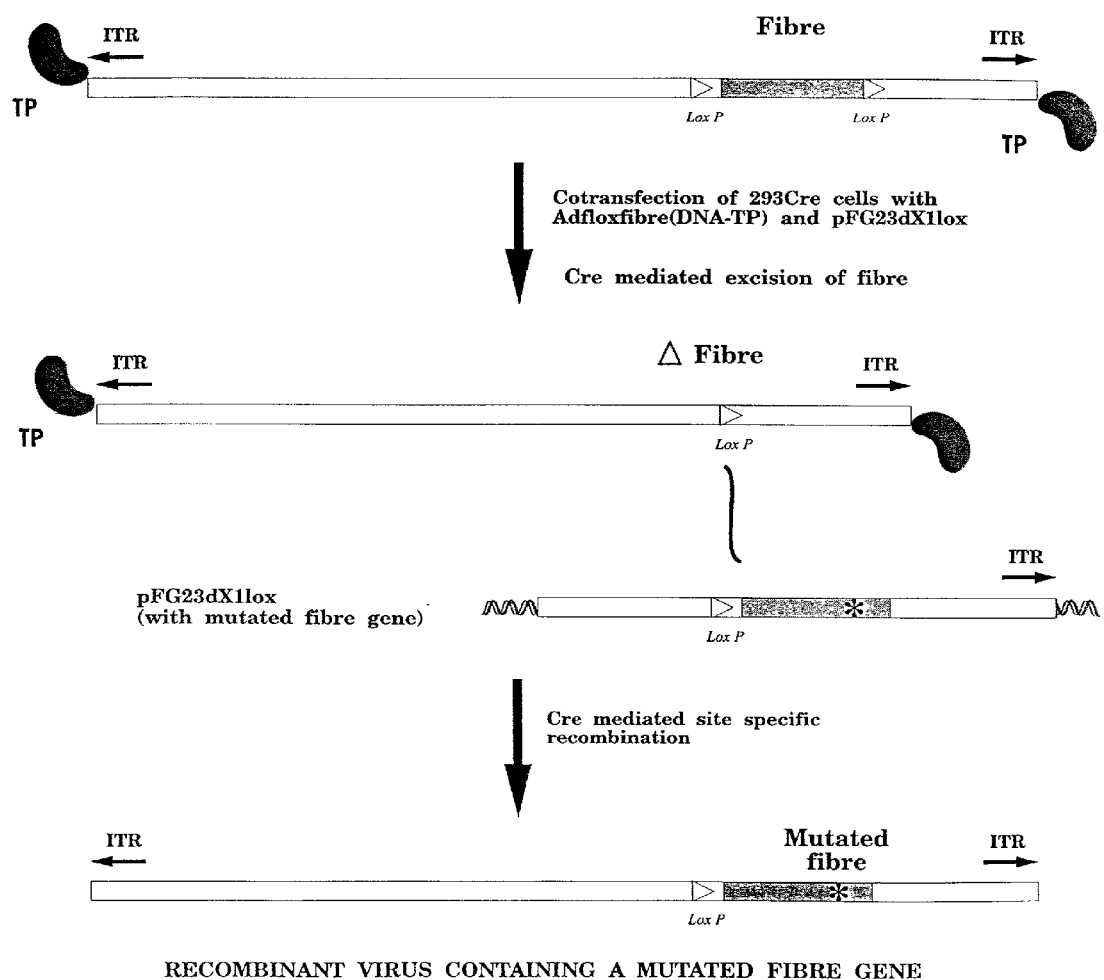

FIG. 12 is a diagrammatic representation showing rescue of a fibre mutation into a virus genome by cotransfection of 293Cre cells with DNA-TP of an Adfloxed fibre and a plasmid containing a lox P site 5' of a (optionally mutated) fibre gene. Viral DNA-TP complex extracted from virus preparations of Adfloxfibre (FIG. 15) and plasmid DNA (pFGdX1lox) optionally carrying a mutated fibre gene are cotransfected into 293Cre cells to produce a recombinant virus expressing the optionally mutated fibre. If desired, viral DNA can be prepared so that the terminal protein remains linked to the ends of the virion DNA as indicated.

Figure 13:
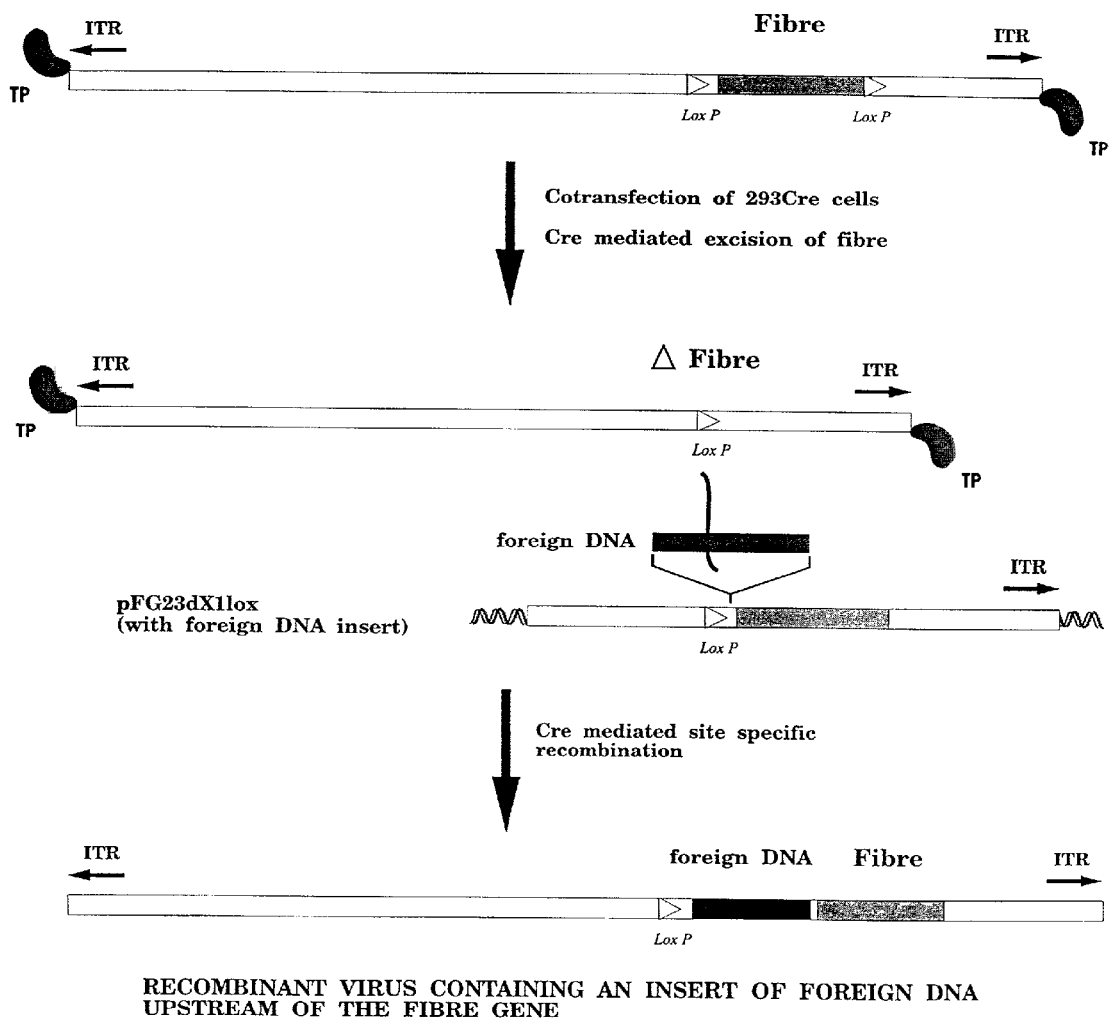

FIG. 13 is a diagrammatic representation showing rescue of a foreign DNA sequence into a virus genome by cotransfection of 293Cre cells with DNA-TP of an Adfloxed fibre and a plasmid containing a lox P site, and a foreign DNA inserted 5' of the fibre gene. Cotransfection of cells with Adfloxfibre DNA-TP and pFG23dX1LacZlox results in production of a vector carrying the foreign (e.g. lacZ) gene inserted upstream of fibre. As noted above in the description of FIG. 8B, the right-most lox site depicted in the Adfloxed fibre genome can be omitted if the DNA-TP is digested with one or more restriction enzymes which cut rightward of the lox site located 5' of fibre.

Figure 14:
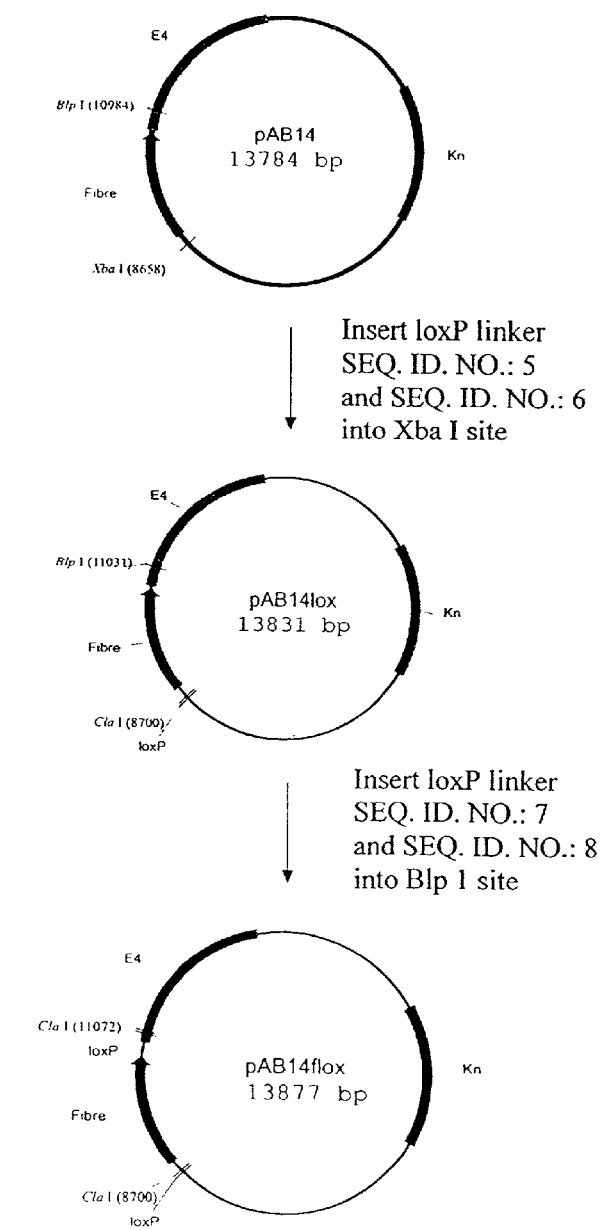

FIG. 14 is a diagrammatic representation showing construction of a plasmid containing a fibre gene with flanking lox P sites. Plasmid pAB14 (described in: Bett, A. J., Prevec, L., and Graham, F. L. Packaging capacity and stability of human adenovirus type 5 vectors. J. Virol. 67: 5911–5921, 1993.) contains Ad sequences from approximately mu 0 to 1.0, 10.6 to 16.1, 69.0 to 78.3, and 85.8 to 100. The plasmid has unique XbaI and BlpI restriction sites suitable for insertion of synthetic oligonucleotides containing lox P sites as illustrated. PAB14flox was constructed by first inserting a lox site into the XbaI site that is upstream of fibre to produce pAB14lox. Subsequently a second lox site was inserted into the unique Blp I site in pAB 14 which is located between the 3' terminus of the fibre gene and the coding regions of E4 genes (pAB14flox: fibre flanked by lox sites).

FIG. 15 is a diagrammatic representation showing isolation of a virus genome containing lox P sites flanking the fibre gene (floxed fibre). Cotransfection of pAB14flox with pFG173 (described in Hanke, T., Graham, F. L., V. Lulitanond and D. C. Johnson. Herpes simplex virus IgG Fc receptors induced using recombinant adenovirus vectors expressing glycoproteins E and I. Virology 177: 437–444, 1990. PFG173 is available from Microbix Biosystems) generates a virus containing a floxed fibre gene, Adfloxfibre.

DETAILED DESCRIPTION OF THE PREFERRED EMBODIMENTS

One embodiment of the present invention provides a bacterial plasmid comprising an antibiotic resistance gene and origin of replication for replication of said plasmid in host cells and further comprising a circularized modified human adenovirus genome that contains sequences that can be recognized and acted upon by the site-specific recombinase such as Cre, FLP or like recombinases. Said bacterial plasmid is designed to be unable to generate infectious adenovirus by virtue of a deletion of viral DNA sequences, such as the packaging signal, which is normally located at the left end of wild-type Ad DNA, and which is essential for virus replication. Alternatively, formation of infectious virus may be prevented by the insertion of DNA ("stuffer DNA") such that the overall size of the resulting virus DNA exceeds the upper packaging limit for Ad virions (approximately 38 kb). Deletion of the pIX sequences from the Ad sequences makes the size-limitation of the packaging limitation more stringent, unless complementing cells which express the pIX gene product are used. Optionally, certain additional viral DNA sequences may be deleted, such as sequences from E3, which can in any event be omitted from the viral genome without preventing a viral genome from replicating in such cells as may be permissive for replication of said viral genome in the form of infectious virus.

Another embodiment of the invention provides a second bacterial plasmid, known as a "shuttle" plasmid, comprising minimally approximately 340 base pairs from the left end of the Ad5 genome, including the left end terminal repeat (ITR) sequences of said genome and the packaging signal sequences thereof, optionally a promoter, and optionally a foreign DNA encoding a protein and optionally a polyadenylation signal, and a lox site (various lox sites are known in the art, including, but not limited to loxP, lox511, lox514, loxPsym, and mention of any one of these sites incorporates the mention of the other lox sites). The promoter, foreign gene and poly adenylation signal are referred to herein collectively as an "expression cassette". Co-transfecting 293Cre cells with said shuttle plasmid and the plasmid of the first embodiment of the invention results in recombination between said plasmids and rescue of said expression cassette into an infectious viral vector by action of said Cre recombinase.

It will be appreciated that the term "bacterial plasmid" is not meant to be limiting, since one skilled 10=in the art would recognize that other types of DNA could be recombined by the Cre recombinase with equal efficiency. For example, the Cre recombinase could be expressed in yeast cells to allow for high-efficiency recombination between yeast artificial chromosomes (YAC's) harboring an Ad genome, or, similarly, in bacteria, to allow for Cre-mediated recombination between cosmids or bacteriophage genomes harboring Ad sequences. Similarly, expression of Cre in mammalian cells could be used to allow for efficient recombination between two or more infectious Ad vectors, between an Ad vector and a bacterial plasmid, between an adenoviral genome and a linear DNA fragment and the like.

A third embodiment of the invention provides a mammalian cell line, such as a human cell line, that provides the Cre recombinase enzyme. Alternatively, Cre maybe provided by an Ad5 derived vector that expresses the Cre protein in suitable cells or Cre may be provided by a third plasmid encoding Cre or optionally Cre could be expressed from an expression cassette inserted into one of the two plasmids used in the two plasmid rescue system. Alternatively, Cre could be expressed in other species, for example bacteria or yeast, to allow for recombination and generation of recombinant Ad genomes in said species. Alternatively, Cre could be provided as a pure or crude protein extract from expression in a variety of species for recombination of said bacterial plasmids in vitro. One skilled in the art would recognize that other recombinase systems are available which could catalyse similar recombination events in place of Cre, for example, not meant to be limiting, the yeast FLP recombinase recognizes and recombines FRT target sites and is therefore expected to provide functions similar to those described herein with reference to Cre and its loxP target sites.

A fourth embodiment of the invention provides an adenovirus or a plasmid containing adenovirus DNA wherein a segment of the viral DNA such as, but not limited to, the region encoding fibre is flanked by lox P sites.

A fifth embodiment of the invention provides an adenovirus or a plasmid containing adenovirus DNA wherein a segment of the viral DNA such as, but not limited to, the region encoding fibre is deleted and substituted by a lox P site.

A sixth embodiment of the invention provides a plasmid containing a portion of the viral genome including a segment of viral DNA comprising, for example, fibre coding sequences wherein a single lox P site is embedded upstream of fibre coding sequences such that Cre-mediated recombination between said plasmid DNA and the plasmid of the fifth embodiment results in production of an infectious viral genome. Optionally the fibre gene in said plasmid may be modified by mutation, insertion or deletion of portions of the fibre coding sequences. Similar plasmids can be constructed that have lox P sites at other locations, depending on the viral DNA segment that is to be manipulated by site-specific recombination. For example, a site exists in the Ad genome between the coding sequences of fibre and the coding sequences of E4 that is suitable for insertion of DNA.

In a seventh embodiment of the invention, plasmids containing adenovirus sequences and lox sites are recombined in the presence of Cre recombinase to generate novel adenovirus mutants containing modifications of the fibre gene or modifications of other viral genes.

In a preferred embodiment of the present invention, a system is described for the construction of novel Ad vectors, or alteration of existing Ad vectors, by the use of a site-specific recombinase.

In a further embodiment of the invention, an infectious viral DNA-TP complex is engineered to take advantage of recombinase-mediated site-specific recombination and the enhanced level of infectivity achieved through presence of the terminal protein.

It will be appreciated by those skilled in the art that the present invention disclosure provides significant advances over techniques known in the art for generation of adenoviral vectors. First, the efficiency by which recombinants are produced is enhanced through use of site-specific recombination, rather than relying exclusively on homologous recombination. Nonetheless, based on the present disclosure, those skilled in the art will appreciate that homologous recombination may be used in combination with the site-specific methodology described herein. This invention further advances the art in that it facilitates use of vectors which are themselves non-infectious and stable. Further, by use of the methods disclosed herein, rapid production of recombinant virus is facilitated wherein every virus produced is a recombinant virus, as opposed to known methods wherein a starting virus is used in a site-specific recombination wherein substantial levels of non-recombinant starting virus remain in the preparation which has to then be serially passaged to remove the contaminating starter virus. As a result of this enhanced efficiency, while it may in many instances be desirable to colony or plaque-purify the results of a given cotransfection, because all viruses produced according to this embodiment of the instant technique are recombinants, plaque purification is not absolutely required. Accordingly, the instant method provides the option of rapid production of recombinants and screening of products, in a "shot-gun" approach, which will provide significant labor and time savings to those skilled in the art.

In reviewing the detailed disclosure which follows, it should be borne in mind that any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting of the invention. For example, the term "gene" includes cDNAs, RNA, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome. In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives is also within the scope of the present invention. "Expression" of a gene or nucleic acid encompasses not only cellular gene expression, but also the transcription and translation of nucleic acid(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence from or into a second nucleic acid sequence. The "target site" of a recombinase is the nucleic acid sequence or region that is recognized (e.g., specifically binds to) and/or acted upon (excised, cut or induced to recombine) by the recombinase. The term "gene product" refers primarily to proteins and polypeptides encoded by other nucleic acids (e.g., non-coding and regulatory RNAs such as tRNA, sRNPs). The term "regulation of expression" refers to events or molecules that increase or decrease the synthesis, degradation, availability or activity of a given gene product.

The present invention is also not limited to the use of the cell types and cell lines used herein. Cells from different tissues (breast epithelium, colon, lymphocytes, etc.) or different species (human, mouse, etc.) are also useful in the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing maybe carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics* 4: 560–569 (1989); Landren et al., *Proc. Natl. Acad. Sci.* 87: 8923–8927 (1990); Barany, F., *Proc. Natl. Acad. Sci.* 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful for interrogating late onset diabetes mutation loci. The elevated reaction temperatures permits the ligation reaction to be conducted with high stringency (Barany, F., *PCR Methods and Applications* 1: 5–16 (1991)).

The hybridization reactions may be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

The detection oligonucleotide probes range in size between 10–1,000 bases. In order to obtain the required target discrimination using the detection oligonucleotide probes, the hybridization reactions are generally run between 20°–60° C., and most preferably between 30°–50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., *Current Protocols in Molecular Biology*, John Wiley and Sons, Baltimore, Md. (1989); Hitt et al, "Construction and propagation of human adenovirus vectors," in *Cell Biology: A Laboratory Handbook*, Ed. J. E. Cells, Academic Press. $2^{nd}$ Edition, Volume 1, pp: 500–512, 1998; Hitt et al, "Techniques for human adenovirus vector construction and characterization," in *Methods in Molecular Genetics*, Ed. K. W. Adolph, Academic Press, Orlando, Fla., Volume 7B, pp: 12–30, 1995; Hitt, et al., "Construction and propagation of human adenovirus vectors," in *Cell Biology: A Laboratory Handbook*," Ed. J. E. Celis. Academic Press. pp: 479–490, 1994, also hereby incorporated by reference. The methods include, for example, stable or transient transfection, lipofection, electroporation and infection with recombinant viral vectors.

The protein products of recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means. Additionally, spleen cells may be harvested from an immunized mouse host and fused to myeloma cells to produce a bank of antibody-secreting hybridoma cells. The bank of hybridomas is screened for clones that secrete immunoglobulins which bind to the variant polypeptides but poorly or not at all to wild-type polypeptides are selected, either by pre-absorption with wild-type proteins or by screening of hybridoma cell lines for specific idiotypes that bind the variant, but not wild-type, polypeptides.

Nucleic acid sequences capable of ultimately expressing the desired variant polypeptides are formed from a variety of different polynucleotides (genomic or cDNA, RNA, synthetic olignucleotides, etc.) as well as by a variety of different techniques.

The DNA sequences are expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally, sequences necessary for replication of a vector.

*E. Coli* is one prokaryotic host useful particularly for cloning DNA sequences of the present invention. Other microbial hosts suitable for use include bacilli, such as *Bacillus subtilus*, and other enterobacteriaceae, such as *Salmonella, Serratia*, and various *Pseudomonas* species. Expression vectors are made in these prokaryotic hosts which will typically contain expression control sequences compatible with the host cell (e.g., an origin of replication). In addition, any number of a variety of well-known promoters are used, such as the lactose promoter system, a tryptophan (Trp) promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. *Saccharomyces* is a suitable host, with suitable vectors having expression control sequences, such a promoters, including 3-phosphoglycerate kinase or other glycolytic enzymes, and an origin of replication, termination sequences, etc. as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobin genes, SV40, Adenovirus, Bovine Papilloma Virus, Herpes Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

The method lends itself readily to the formulation of test kits for use in diagnosis. Such a kit comprises a carrier compartmentalized to receive in close confinement one or more containers wherein a first container contains reagents useful in the localization of the labeled probes, such as enzyme substrates. Still other containers contain restriction enzymes, buffers etc., together with instructions for use.

The methods provided herein for obtention of recombinant Ad vectors are significantly different from previously described methods that rely on homologous recombination catalysed by recombinases in host cells or that rely on in vitro ligation of viral DNA fragments to produce infectious viral DNA. For viral DNA replication and packaging of viral DNA into virion particles, only three regions of the viral DNA are known to be required in cis. These are the left inverted terminal repeat, or ITR, (bp 1 to approximately 103) the packaging signals (approximately 194 to 358 bp) (Hearing and Shenk, 1983, Cell 33: 695–703; Grable and Hearing 1992, J. Virol. 64: 2047–2056) and the right ITR. Among the regions of the viral genome that encode proteins that function in trans, two have been most important in the design and development of adenovirus vectors. These are early region 3 (E3) located between approximately 76 and 86 mu (mu=% distance from the left end of the conventionally oriented genome) and early region 1 (E1) located between approximately 1 and 11 mu. E3 sequences have long been known to be nonessential for virus replication in cultured cells and many viral vectors have deletions of E3 sequences so that the capacity of the resulting vector backbone for insertion of foreign DNA is thereby increased significantly over that allowable by the wild-type virus (Bett, A. J., Prevec, L., and Graham, F. L. Packaging capacity and stability of human adenovirus type 5 vectors. J. Virol. 67: 5911–5921, 1993.). E1 encodes essential functions. However, E1 can also be deleted, providing that the resulting virus is propagated in host cells, such as the 293 cell line, PER-C6 cells, 911 cells, and the like, which contain and express E1 genes and can complement the deficiency of E1(−) viruses.

Viruses with foreign DNA inserted in place of E1 sequences, and optionally also carrying deletions of E3 sequences are conventionally known as "first generation" adenovirus vectors. First generation vectors are of proven utility for many applications. They can be used as research tools for high-efficiency transfer and expression of foreign genes in mammalian cells derived from many tissues and from many species. First generation vectors can be used in development of recombinant viral vaccines when the vectors contain and express antigens derived from pathogenic organisms. The vectors can be used for gene therapy, because of their ability to efficiently transfer and express foreign genes in vivo, and due to their ability to transduce both replicating and nonreplicating cells in many different tissues. Adenovirus vectors are widely used in these applications.

There are many known ways to construct adenovirus vectors. As discussed above, one of the most commonly employed methods is the so called "two plasmid" technique. In that procedure, two noninfectious bacterial plasmids are constructed with the following properties: each plasmid alone is incapable of generating infectious virus. However, in combination, the plasmids potentially can generate infectious virus, provided the viral sequences contained therein are homologously recombined to constitute a complete infectious virus DNA. According to that method, typically one plasmid is large (approximately 30,000–35,000 nt) and contains most of the viral genome, save for some DNA segment (such as that comprising the packaging signal, or encoding an essential gene) whose deletion renders the plasmid incapable of producing infectious virus. The second plasmid is typically smaller (eg 5000–10,000 nt), as small size aids in the manipulation of the plasmid DNA by recombinant DNA techniques. Said second plasmid contains viral DNA sequences that partially overlap with sequences present in the larger plasmid. Together with the viral sequences of the larger plasmid, the sequences of the second plasmid can potentially constitute an infectious viral DNA. Cotransfection of a host cell with the two plasmids produces an infectious virus as a result of homologous recombination between the overlapping viral DNA sequences common to the two plasmids. One particular system in general use by those skilled in the art is based on a series of large plasmids known as pBHG10, pBHG11 and pBHGE3 described by Bett, A. J., Haddara, W., Prevec, L. and Graham, F. L: "An efficient and flexible system for construction of adenovirus vectors with insertions or deletions in early regions 1 and 3," Proc. Natl. Acad. Sci. US 91: 8802–8806, 1994 and in U.S. Pat. No. 6,140,087 (hereby incorporated by reference). Those plasmids contain most of the viral genome and are capable of producing infectious virus but for the deletion of the packaging signal located at the left end of the wild-type viral genome. The second component of that system comprises a series of "shuttle" plasmids that contain the left approximately 340 nt of the Ad genome including the packaging signal, optionally a polycloning site, or optionally an expression cassette, followed by viral sequences from near the right end of E1 to approximately 15 mu or optionally to a point further rightward in the genome. The viral sequences rightward of E1 overlap with sequences in the pBHG plasmids and, via homologous recombination in cotransfected host cells, produce infectious virus. The resulting viruses contain the packaging signal derived from the shuttle plasmid, as well as any sequences, such as a foreign DNA inserted into the polycloning site or expression cassette located in the shuttle plasmid between the packaging signal and the overlap sequences. Because neither plasmid alone has the capability to produce replicating virus, infectious viral vector progeny can only arise as a result of recombination within the cotransfected host cell. However, as has been noted above, such homologous recombination processes can be inefficient, resulting in variable success in the isolation of vectors and occasional failure, particularly in the hands of those who are not specifically skilled in the art of virology, and more particularly, in the art of adenovirology.

Site-specific recombination catalysed by an efficient recombinase, such as the Cre or FLP recombinase, can be many fold more efficient than homologous recombination. This invention disclosure provides methods and nucleic acid constructs which significantly enhance the ease of production of viral vectors by the two plasmid method by enabling site-specific recombination between individual nucleic acids constructs, neither of which alone is able to replicate and produce infectious adenovirus. The methodology described herein furthermore utilizes Cre-loxP and other known recombination systems for efficient introduction of mutations of viral genes into the viral genome. Furthermore, the instant methodology is also applicable to insertion of foreign DNA sequences into various regions of the viral DNA, in addition to the E1 region classically used for that purpose. In additional embodiments of this invention, site-specific recombination is utilized in combination with infectious viral DNA having covalently bound terminal protein (DNA-TP complex), at either or both 5' strands of the DNA (i.e. either the coding or non-coding strand). Additional embodiments and applications of the site-specific recombination methodology will also become apparent based on the instant disclosure.

Having generally described the purposes, advantages, applications and methodology of this invention, the following specific examples are provided to describe in a detailed fashion, various embodiments of this invention. However, it should be appreciated that the invention described herein is not limited to the specifics of the following examples, which are provided merely as a guide for those wishing to practice this invention. The scope of the invention is to be evaluated with reference to the complete disclosure and the claims appended hereto.

The following examples using the human adenovirus serotype 5 are not meant to be limiting. One skilled in the art would realize that similar plasmids, viruses and techniques could be utilized with a different human adenovirus serotype, for example Ad2. Similarly, the use of human Ads is not meant to be limiting since similar plasmids, viruses and techniques could be utilized for different non-human adenoviruses, for example bovine. Similarly, the use of adenoviruses is not meant to be limiting since similar plasmids, viruses and techniques could be utilized with other viruses, both human and non-human, for example baculovirus.

Use of Cre recombinase in these and other examples is not meant to be limiting as a person skilled in the art will readily appreciate that other enzymes capable of catalysing site-specific recombination between DNA sequences recognized by said enzymes could equally be employed in place of the Cre recombinase. An example, not meant to be limiting, of such an enzyme that could be substituted for Cre is the "FLP" recombinase of yeast in combination with its target site FRT (O'Gorman et al. Science 251, 1351, 1991).

A component of the invention is the use of human cells, such as 293 cells or other cells that may be deemed suitable in that they support the replication of the viral components of the invention, that express Cre recombinase and that can be transfected with the plasmids described herein and in the examples which follow, to generate a virus containing the desired modifications such as an insertion of foreign DNA or a modified fibre gene. It will be appreciated by those skilled in the art that the requisite cell lines can be generated by transfecting 293 cells or other cells, with a plasmid comprising the coding sequences for Cre under the control of suitable regulatory sequences, including a promoter and polyadenylation signal and containing, in addition, a selectable gene encoding, for example, resistance to G418 or histidinol. A person skilled in the art can readily obtain drug resistant cells that express the Cre recombinase in addition to the drug resistance gene used for selection. It will also be appreciated by one skilled in the art, based on the present disclosure, that host cells can also be induced to transiently express a recombinase by transfection with a plasmid comprising an expression cassette containing said recombinase gene or by infection with a viral vector that expresses the recombinase. Thus the example of 293Cre cells or other permanently transformed recombinase expressing cell lines is not meant to be limiting.

EXAMPLE 1

Two-plasmid, Site-specific Adenovral Recombination

Figure 1:
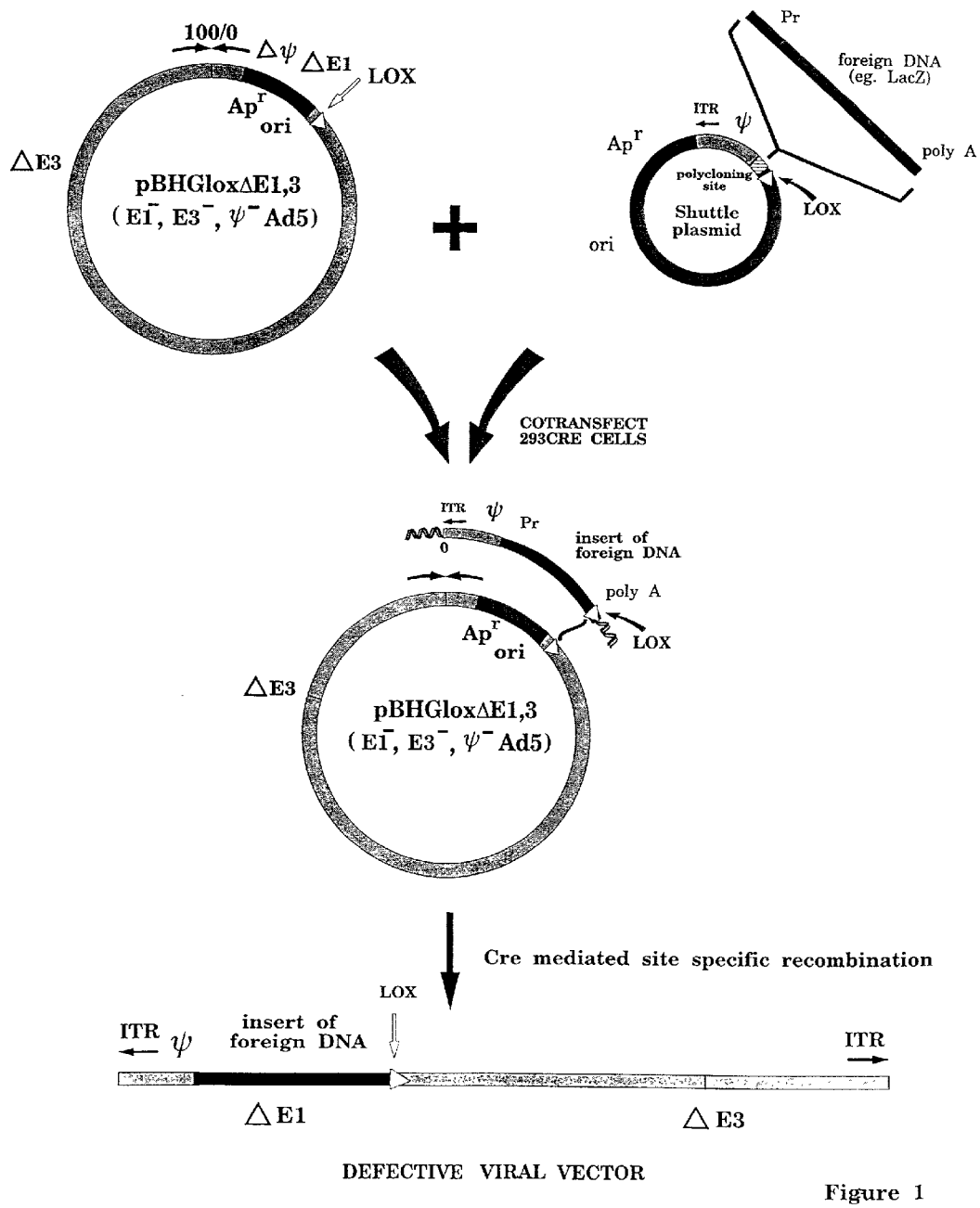
FIG. 1 is a diagrammatic representation showing a method for isolation of an Ad vector containing an expression cassette in E1 using the Cre/lox recombination system. pBHG10lox comprises a circularized form of the Ad genome with a deletion of the E1 region including the packaging signal and a bacterial plasmid origin of replication and an ampicillin resistance gene. The plasmid has a loxP site near the 5' end of the pIX gene of the Ad genome and a deletion of E3 sequences. The "shuttle plasmid" contains an ITR of the virus genome and a packaging signal, a polycloning site for insertion of a foreign DNA (eg bacterial β-galactosidase (LacZ)) and a loxP site inserted in the same relative orientation as the loxP site in pBHG10lox. Cotransfection of these two plasmids into 293Cre cells that express Cre results in Cre-mediated recombination and formation of joint molecules that generate infectious viruses containing the foreign DNA insert.

FIG. 1 provides a graphic representation of the use of a plasmid, pBHG10lox, which comprises a circularized form of the Ad genome in which part or all of the E1 region, including the packaging signal, is substituted by sequences comprising a bacterial plasmid origin of replication and an antibiotic resistance gene, such as that encoding ampicillin resistance. The plasmid further comprises a loxP site near the 5' end of the pIX gene of the Ad genome. The plasmid may also, optionally, have a deletion of E3 sequences (as shown in this illustration by the symbol Δ3) which may optionally be substituted with one or more unique cloning sites for insertion of foreign DNA in the ΔE3 region.

A second component of the invention comprises a "shuttle plasmid" containing an ITR of the virus genome and a packaging signal, a polycloning site into which may be inserted a foreign DNA such as that encoding for bacterial β-galactosidase (LacZ) or any other gene, expression of which is desired either in a gene therapeutic or vaccine context, and a loxP site inserted in the same relative orientation as the loxP site in pBHG10lox. To obtain high-efficiency rescue of the foreign DNA into an infectious viral vector, the two plasmids are cotransfected into human cells, such as 293Cre cells, PER-C6 cells, 911 cells, and the like, engineered to express Cre and which, in addition, express the E1 region of the Ad genome. It should be appreciated that the manner of provision of the recombinase is not critical. The recombinase may be constitutively expressed by the cell into which the two plasmids are introduced. The recombinase may be provided in trans, via a third plasmid, or in cis, by inclusion of a recombinase expression cassette in one of the introduced plasmids. In addition, it will be appreciated that any recombinase which efficiently induces site-specific recombination between sequences present on the two plasmids may be employed according to this methodology. Thus, the FLP recombinase, which recognizes the sequences known as FRT, may be used in place of the Cre/loxP combination, and thus, wherever Cre or loxP are mentioned herein, such mention should be read to include any other site-specific recombination system now known or henceforth discovered, when applied to the specific techniques disclosed and claimed herein.

Cre-mediated recombination results in formation of joint molecules that generate infectious viruses containing the foreign DNA insert. Because pBHG10lox lacks the viral packaging signal, the only viruses that can form are those containing the packaging signal and foreign DNA of the shuttle plasmid. These are generated in large numbers because of the high-efficiency and specificity of Cre recombinase, and there is no background of non-recombinant virus which, according to a method such as that of Hardy et al., J. Virol. 71(3):1842–1849, (1997), even after three sequential passages in Cre expressing cells, results in a vector preparation still contaminated by starting (non-recombinant) virus.

EXAMPLE 2

Comparison of Homologous and Site-Specific Recombination

Figure 2:
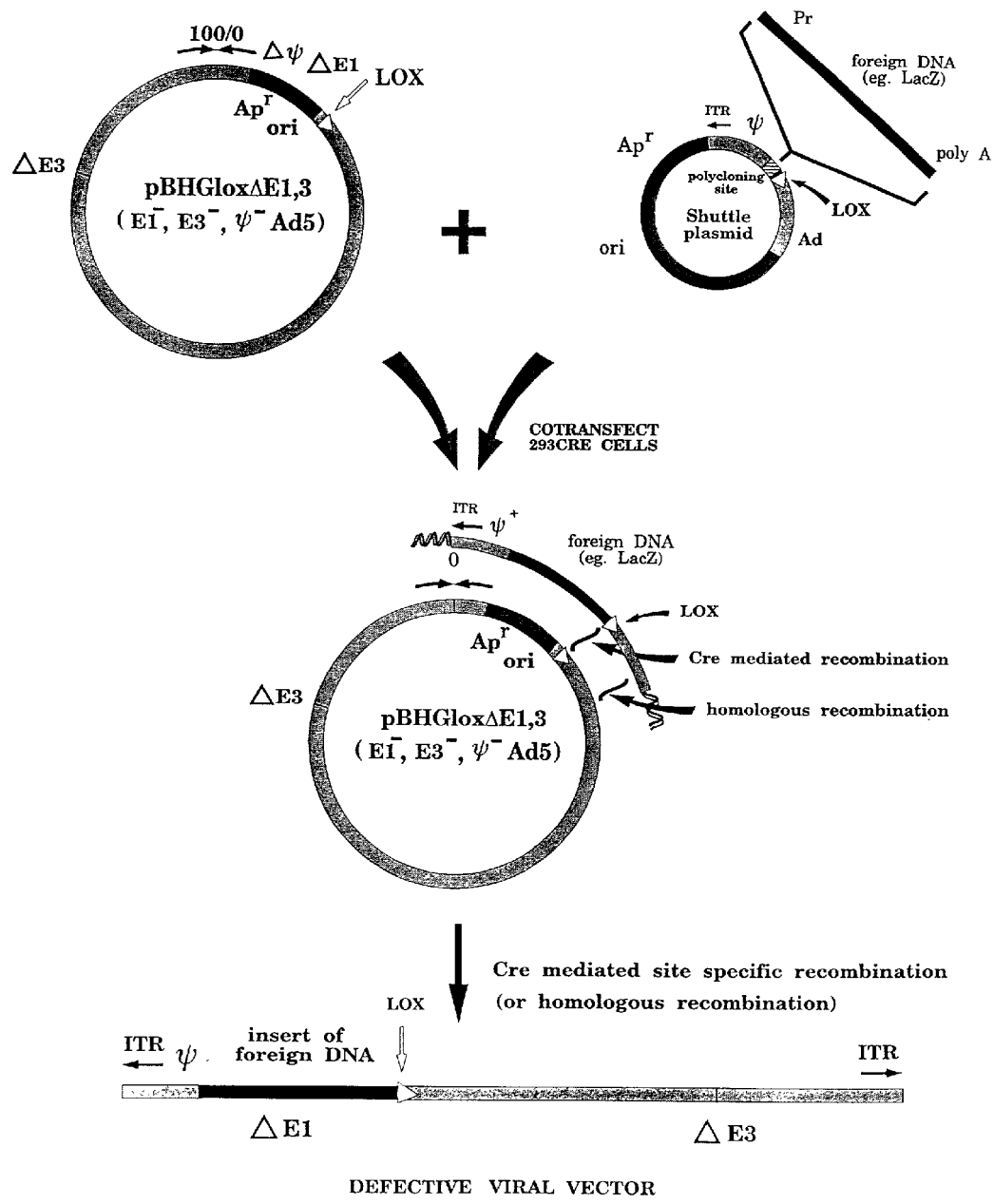
FIG. 2 illustrates a cotransfection experiment similar to that depicted in FIG. 1 except that the shuttle plasmid contains Ad sequences 3' of the lox site that overlap (are homologous) with viral sequences in pBHG10lox to the right of the lox site. Therefore an Ad vector containing an expression cassette in E1 can be generated by Cre/lox recombination when the two plasmids are cotransfected into 293 Cre cells or alternatively by homologous recombination between overlapping sequences. The shuttle plasmid in the illustration permits a comparison of the efficiency obtainable from the two recombination modes.

FIG. 2 illustrates use of a modified shuttle plasmid wherein Ad sequences from about 10 mu to about 15 mu are present to the right of the lox site. These sequences permit homologous recombination to occur in the absence or presence of Cre. A shuttle plasmid such as that shown in this figure is generally used only for comparison purposes to assess the relative efficiency of homologous versus Cre-mediate recombination. As will be seen in the subsequent description of the invention, in the presence of Cre, overlapping sequences are unnecessary and can be omitted, although this disclosure does not require the absence of such sequences.

EXAMPLE 3

Sequences Useful in the Production of Plasmids which may be Recombined in a Site-Specific Manner to Produce Adenoviral Vectors FIG. 3 illustrates sets of oligonucleotides used in various cloning procedures. The double stranded oligonucleotide (SEQ ID NO:1 and SEQ ID NO: 2; AB3233/3234) contains a loxP site with restriction sites for ScaI and EcoRI at one end of the oligo outside of the loxP region. When annealed, the oligonucleotides have BamHI/BglII overhangs which are designed for cloning into and concomitant destruction of the BglII site. The internal ScaI site found in (SEQ ID NO:1 and SEQ ID NO: 2; AB3233/3234) was designed to facilitate determination of the orientation of the linker and also for subsequent deletion of Ad5 sequences from m.u. 9.8–15.8. The second linker (SEQ ID NO:3 and SEQ ID NO:4; AB14626/14627) has EcoRI and SalI overhangs and a multiple cloning region containing SmaI, BglII, HindIII and ScaI restriction sites.

EXAMPLE 4

Construction of Bacterial Plasmids Containing Circularized Forms of the Adenovirus Genome Suitable for Rescue of Viral Vectors Using Site-Specific Recombination According to the General Scheme Illustrated According to FIG. 1

Figure 4A:
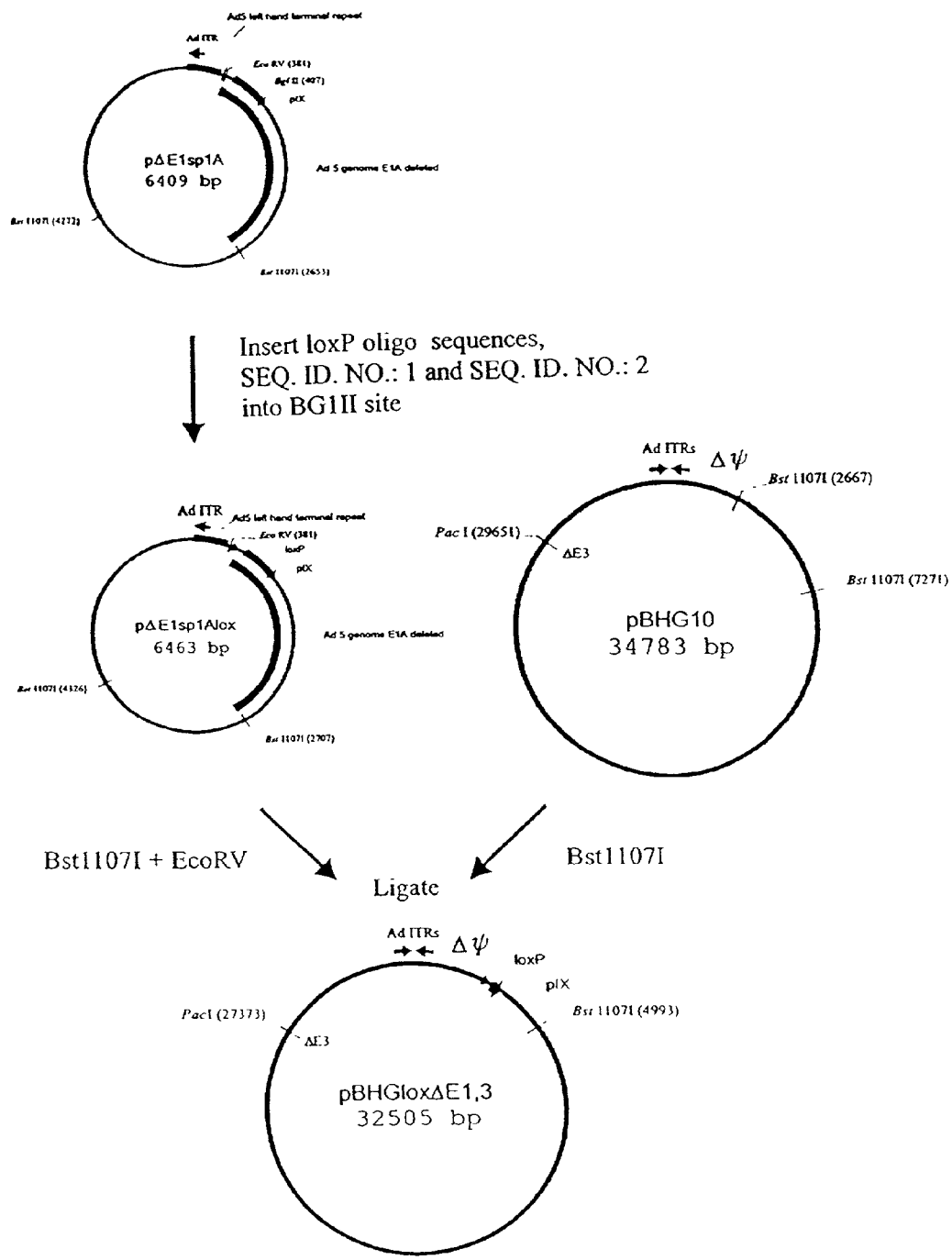
FIG. 4A illustrates the construction of a plasmid, derived from pBHG10 (Bett, A. J., Haddara, W., Prevec, L. and Graham, F. L "An efficient and flexible system for construction of adenovirus vectors with insertions or deletions in early regions 1 and 3." Proc. Natl. Acad. Sci. US 91: 8802–8806, 1994., available from Microbix Biosystems), wherein a loxP site is inserted at the 3' end of an E1 deletion and 5' (upstream) of the pix gene. pBHG10lox was constructed by replacing the 4604 bp Bst1107I fragment from pBHG10 with the 2326 bp EcoRV/Bst1107I fragment from pΔE1sp1Alox (see FIG. 5). Foreign DNA sequences can be inserted into the unique PacI site of pBHG10lox for rescue of genes in E3.

FIG. 4A illustrates production of a plasmid, pBHG10lox, a derivative of pBHG10, modified to contain a loxP site at the 3' end of the E1 deletion. As can be seen with reference to the figure, this plasmid was constructed by replacing the 4604 bp Bst1107I fragment from pBHG10 with the 2326 bp EcoRV/Bst1107I fragment from pΔE1sp1Alox. The plasmid pΔE1sp1Alox (FIG. 5) was constructed by inserting an oligonucleotide bearing a loxP site (comprised of annealed oligos (SEQ ID NO:1 and SEQ ID NO: 2; AB3233/3234) into the BglII site of pΔE1sp1A. Foreign sequences can be inserted into the unique PacI site of pBHG10lox for rescue of genes in E3. The plasmid illustrated in FIG. 4 can be selected from the series pBHG10 (as illustrated), pBHG11, pBHGE3, or like plasmid, for modification to contain a lox P site near the 3' end of E1 ie. near the 5' end of the pIX gene at approximately nt 3520 in the conventional sequence of Ad5. Optionally E1 sequences from approximately nt 188 to approximately 3520 may be deleted from said plasmid. Like the parental plasmid (such as pBHG10, pBHG11 or pBHGE3) the modified pBHG derivative (eg. pBHG10lox, pBHG11lox, pBHGE3lox, or like plasmid) lacks the packaging signal (ψ), and is consequently incapable of producing infectious virus in transfected host cells.

Figures 1, 4B:
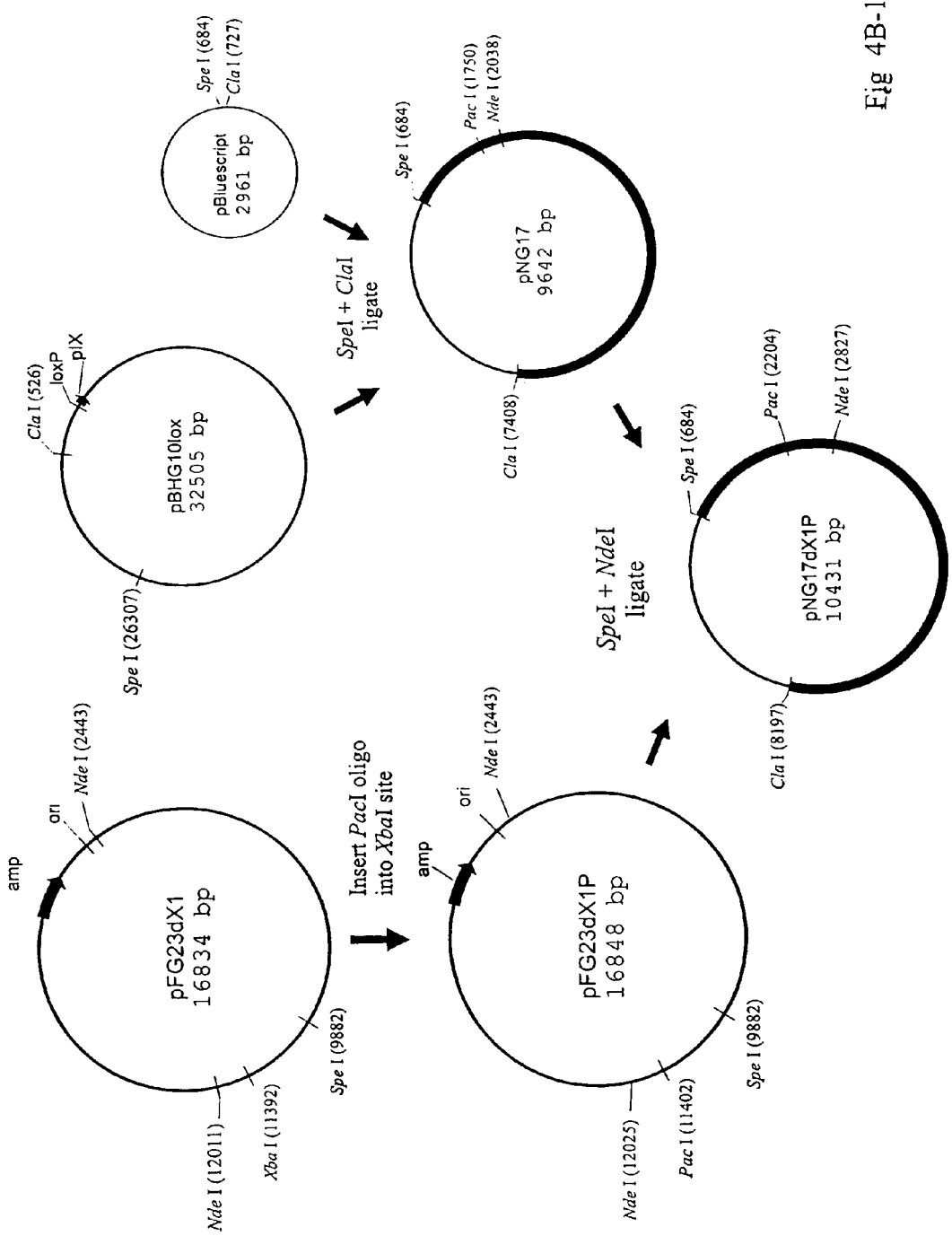
Figures 2, 4B:
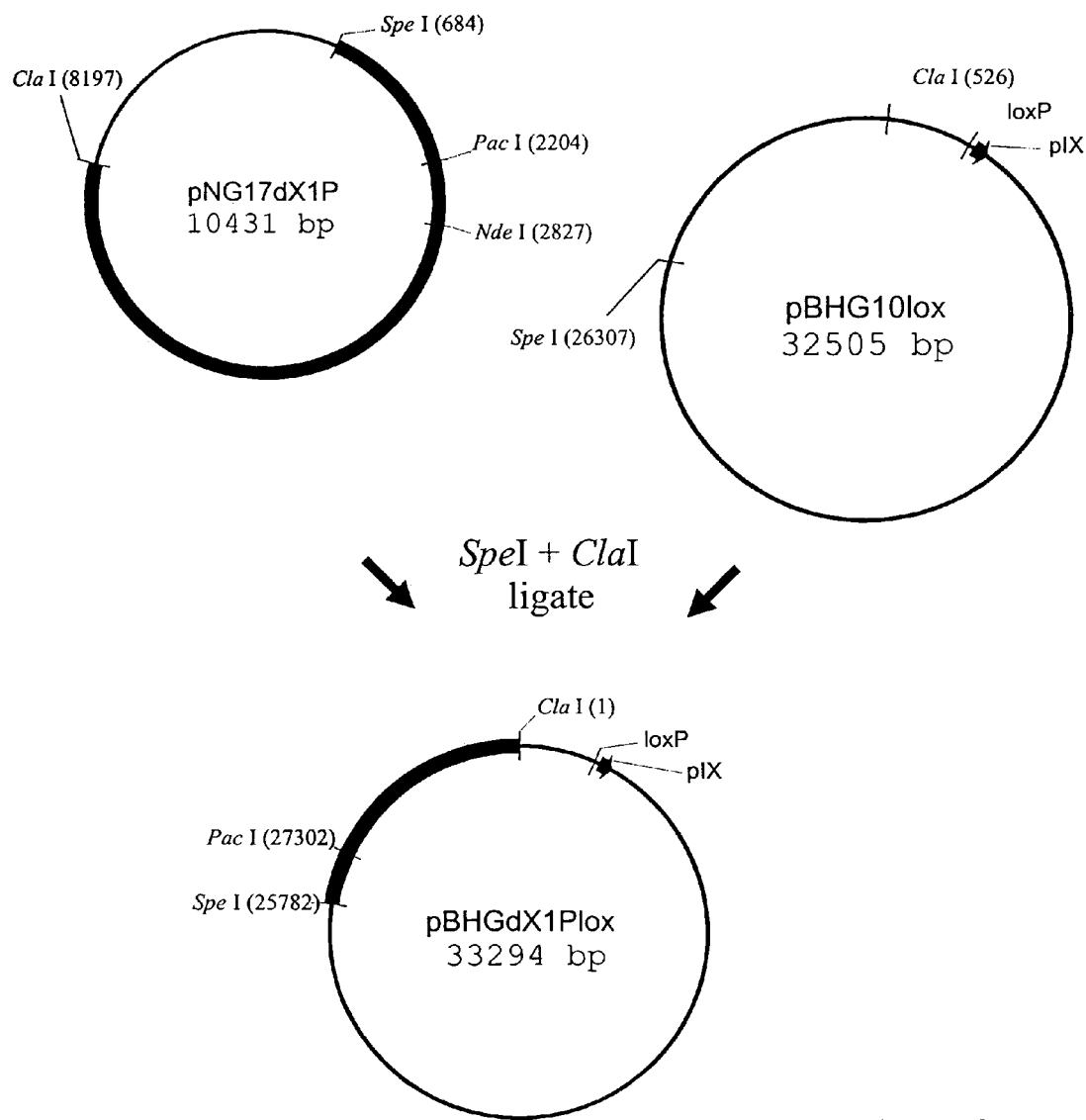

FIGS. 4B-1 and 4B-2 illustrate the construction of a plasmid, pBHGdX1Plox, containing a modified E3 deletion (taken from pFG23dX1) and a lox site 5' of the pIX gene. The plasmid pFG23dX1P was constructed by inserting an oligonucleotide containing a PacI site (AB 14566; 5'-CTAGCTTAATTAAG -3', SEQ ID NO.:9) into the XbaI site of pFG23dX1. The plasmid pNG17 was constructed by cloning the 6724 bp SpeI/ClaI fragment from pBHG 10lox into pBluescript. The plasmid pNG17dX1P was constructed by replacing the 1354 bp SpeL/NdeI fragment from pNG17 with the 2129 bp SpeI/NdeI fragment from pFG23dX1P. The plasmid pBHGdX1P was constructed by replacing the 6724 bp SpeI/ClaI fragment from pBHG 10lox with the 7495 bp SpeI/ClaI fragment from pNG17dX1P.

Figure 4C:
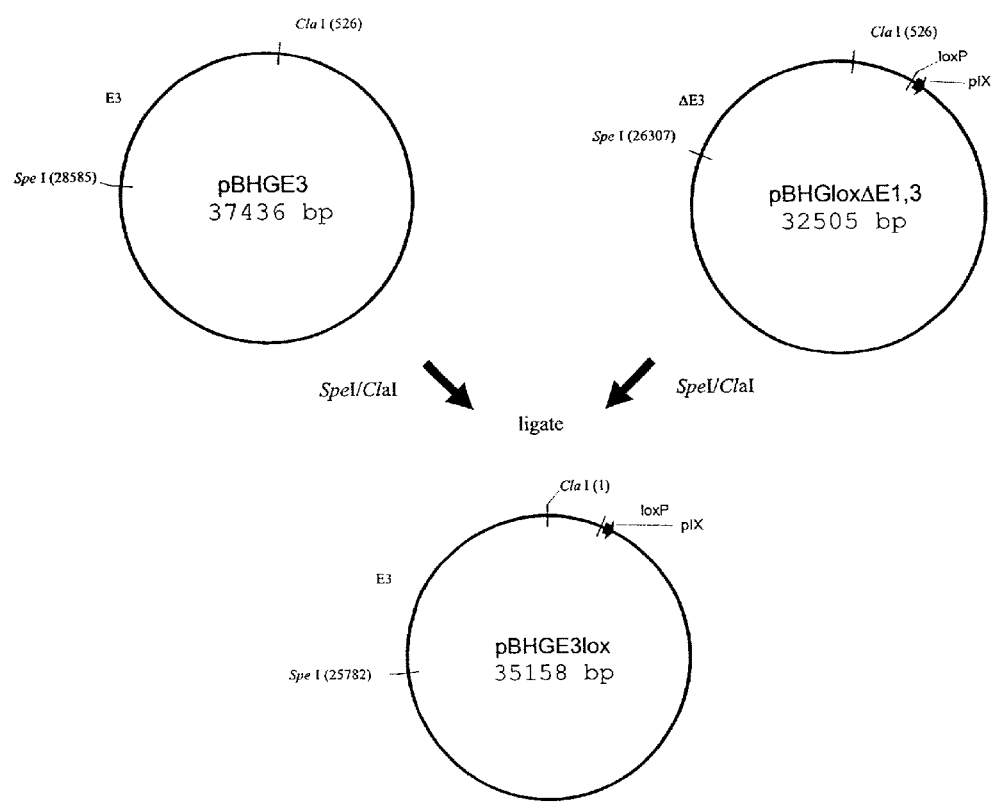
FIG. 4C illustrates the construction of pBHGE3lox, a plasmid derived from pBHGE3 and pBHG10lox constructed by replacing the 6724 bp SpeI/ClaI fragment from pBHG10lox with the 9377 bp SpeI/ClaI fragment from pBHGE3. PBHGE3 lox contains a complete E3 region for isolation of viral vectors that retain a wild-type E3.

FIG. 4C illustrates the construction of a plasmid containing a wild-type E3 region and a loxP site 5' of the pIX gene. The plasmid pBHGE3 lox was constructed by replacing the 6724 bp SpeI/ClaI fragment from pBHG10lox with the 9377 bp SpeI/ClaI fragment from pBHGE3.

EXAMPLE 5

Construction of Shuttle Plasmids for Recombination with Adenoviral Rescue Plasmids Constructed According to Example 4

As described above, a second embodiment of the invention comprises a shuttle plasmid selected from a series of plasmids containing, minimally: the left end of the viral genome including all or most of the left inverted Terminal Repeat (ITR nts 1–103 of the Ad 5 DNA) and the packaging sequence, and optionally a polycloning site or optionally an expression cassette. With reference to FIGS. 5—8, such shuttle plasmids are modified to contain a lox P site in the same orientation as the loxP site in the pBHG derivative, (see Example 4, referred to herein as the "rescue plasmid"), said loxP site being positioned in said shuttle plasmid to the right of said polycloning site or said expression cassette.

Figure 5:
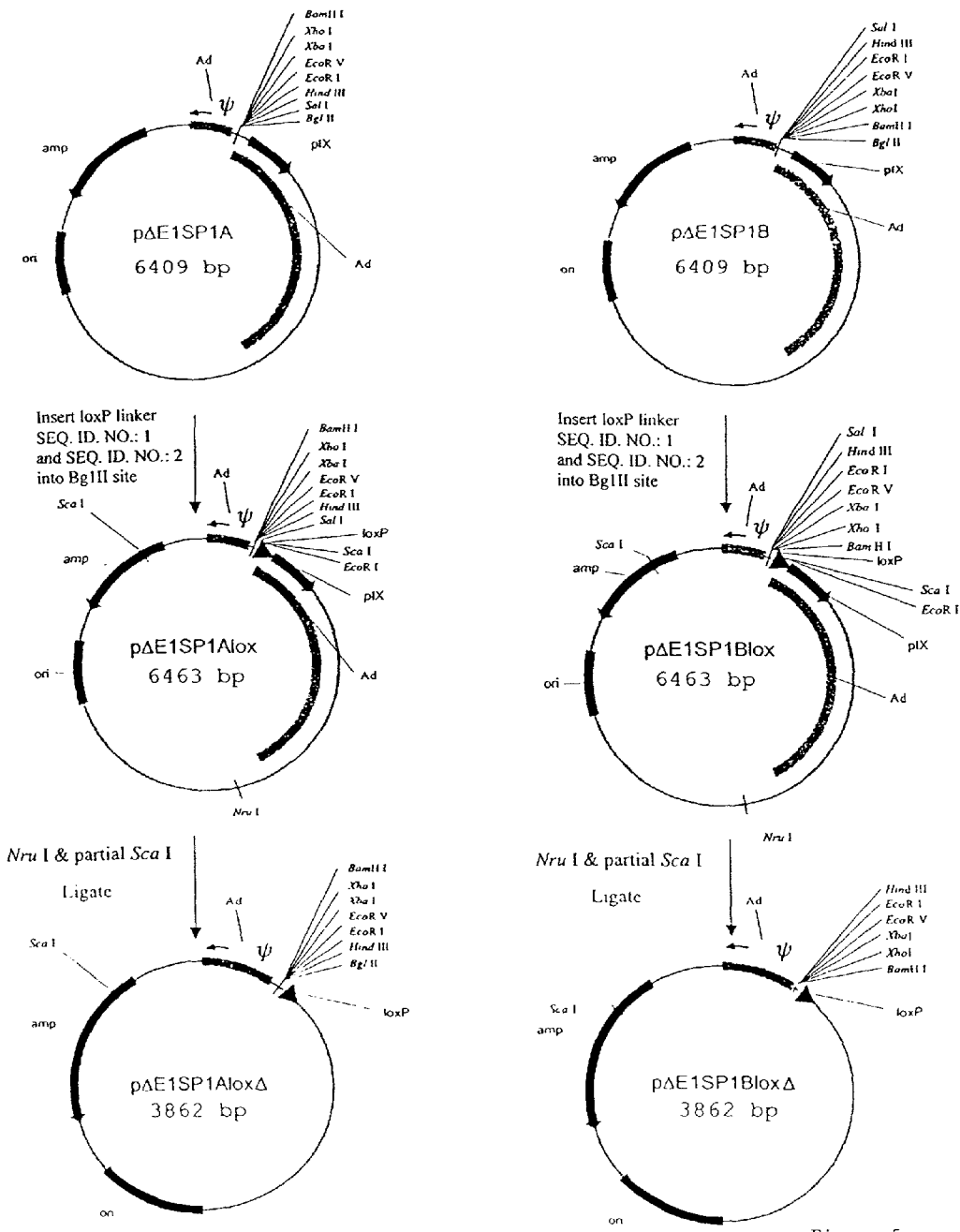
FIG. 5 illustrates the construction of shuttle plasmids derived from pΔE1SP1A and pΔE1SP1B wherein a loxP site is introduced 3' of the packaging signal. The plasmids pΔE1sp1Alox and pΔE1sp1Blox were constructed by inserting an oligonucleotide bearing a loxP site (comprised of SEQ ID NO:1 and SEQ ID NO:2 annealed oligonucleotide sequences, also identified as AB3233 and AB 3234) into the BglII site of pΔSE1sp1A. Subsequent digestion with Nru I and partial Sca I digestion followed by ligation generated pΔE1SP1AloxΔ and pΔE1SP1BloxΔ.

FIG. 5 illustrates the construction of shuttle plasmids derived from pΔE1SP1A and pΔE1SP1B wherein loxP sites are introduced 5' of the pIX gene. The plasmids, pΔSE1sp1A and pΔE1SPLB are left end shuttle plasmids containing Ad5 sequences from m.u. 0–15.8 with E1 sequences deleted between m.u. 1 and 9.8. They are identical except that the restriction sites in the multiple cloning region are reversed. A synthetic loxP linker (SEQ ID NO:1 and SEQ ID NO:2; AB3233/3234) was introduced into the BglII site of each plasmid generating pΔE1SP1Alox and pΔE1SP1Blox. Ad5sequences from m.u. 9.8–15.8 were removed by digesting the plasmids with NruI, partially cutting with ScaI followed by self-ligation. The plasmids thus generated are called pΔE1SP1AloxΔ and pΔE1SP1BloxΔ.

Figure 6A:
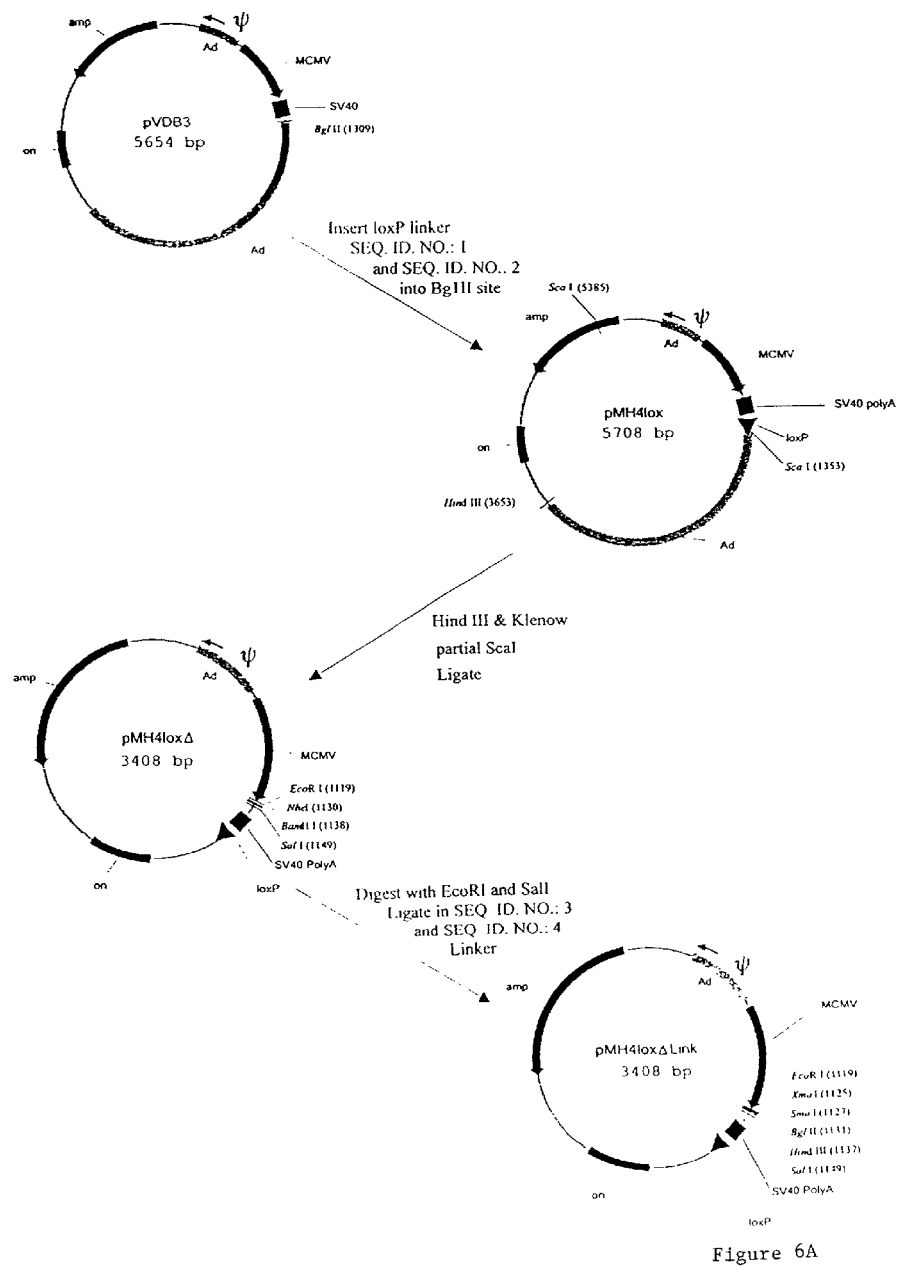
FIG. 6A illustrates the construction of pMH4lox, pMH4loxΔ and pMH4loxΔlink plasmids that contain lox sites and a promoter and polyadenylation signal and polycloning sites for insertion of foreign DNA to produce expression cassettes in which transcription is driven by the murine cytomegalovirus immediate early gene promoter. Plasmid pVDB3 (see FIG. 6a) is derived from pMH4 but contains a pUC based origin of replication rather than a pBR322 origin. It contains Ad5 sequences from m.u. 0–15.8 with E1 sequences deleted between m.u. 1 and 9.8 and substituted with an expression cassette: a 0.5 kbp (−491 to +36) fragment of the MCMV IE promoter, unique restriction enzyme sites for cloning (Eco RI, Nhe I, Bam HI and Sal I) followed by an SV40 polyadenylation signal. To make pMH4lox, a loxP linker (SEQ ID NO:1 and SEQ ID NO: 2; AB3233/3234) was introduced into the Bg/II site of pVDB3. Ad5 sequences m.u. 9.8–15.8 were deleted from pMH4lox by digesting with Hind III, treating with the Klenow fragment of E. coli DNA polymerase then partially digesting with Sca I followed by self-ligation. The resulting shuttle plasmid, pMH4loxΔ, can be used with pBHG10lox to produce Ad vectors via Cre/lox mediated recombination. To make pMH4loxΔ a more flexible plasmid for cloning purposes, a linker (SEQ ID NO:3 and SEQ ID NO:4; AB14626/14627) containing a different multiple cloning region was introduced between the Eco RI and Sal I sites resulting in pMH4loxΔlink.

FIG. 6A illustrates the construction of pMH4lox and pMH4loxΔ plasmids that contain a promoter and polyadenylation signal and polycloning sites for insertion of foreign DNA to produce expression cassettes in which transcription is driven by the murine cytomegalovirus immediate early gene promoter. Plasmid pVDB3 is derived from pMH4 but contains a pUC-based origin of replication, rather than a pBR322 origin. It contains Ad5 sequences from m.u. 0–15.8 with E1 sequences deleted between m.u. 1 and 9.8 and subsituted with an expression cassette: a 0.5 kbp (−491 to +36) fragment of the MCMV IE promoter, unique restriction enzyme sites for cloning (Eco RI, Nhe I, Bam HI and SalI) followed by an SV40 polyadenylation signal. To make pMH4lox, a loxP linker (SEQ ID NO:1 and SEQ ID NO:2; AB3233/3234) was introduced into the BglII site of pVDB3. Ad5 sequences m.u. 9.8–5.8 were deleted from pMH4lox by digesting with Hind III, treating with the Klenow fragment of E. coli DNA polymerase then partially digesting with Sca I followed by self-ligation. The resulting shuttle plasmid, pMH4loxΔ, can be used with pBHG10lox to produce Ad vectors via Cre/lox mediated recombination. To make pMH4loxΔ a more flexible plasmid for cloning purposes, a linker (SEQ ID NO:3 and SEQ ID NO:4; AB 14626/14627), containing a different multiple cloning region, was introduced between the Eco RI and Sal I sites resulting in pMH4loxΔlink.

Figure 6B:
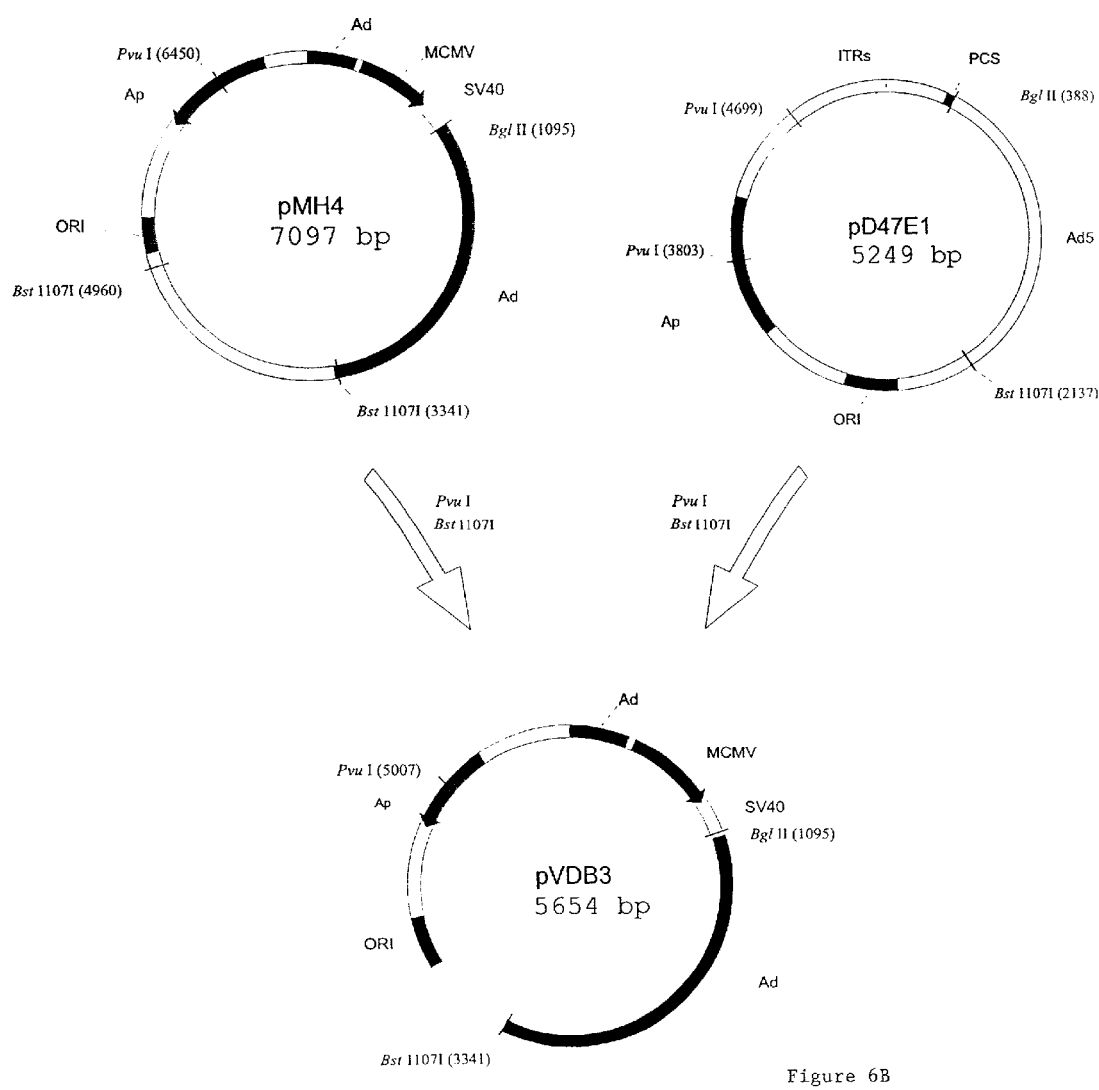
FIG. 6B illustrates the construction of plasmid pVDB3 derived from pMH4 but containing a pUC based origin of replication rather than a pBR322 origin. A PvuI to Bst 1 1071 fragment from pMH4 (Microbix Biosystems) was ligated to a Bst 11071 to Pvu I fragment from pD47E1 containing a pUC based (pNEB193, New England Biolabs) origin of plasmid DNA replication to generate pVDB3.

FIG. 6B illustrates the construction of plasmid pVDB3. A PvuI to Bst 11071 fragment from pMH4 (Microbix Biosystems) was ligated to a Bst 11071 to Pvu I fragment from pD47E1 containing a pUC-based (pNEB193, New England Biolabs) origin of plasmid DNA replication to generate pVDB3.

Figure 7:
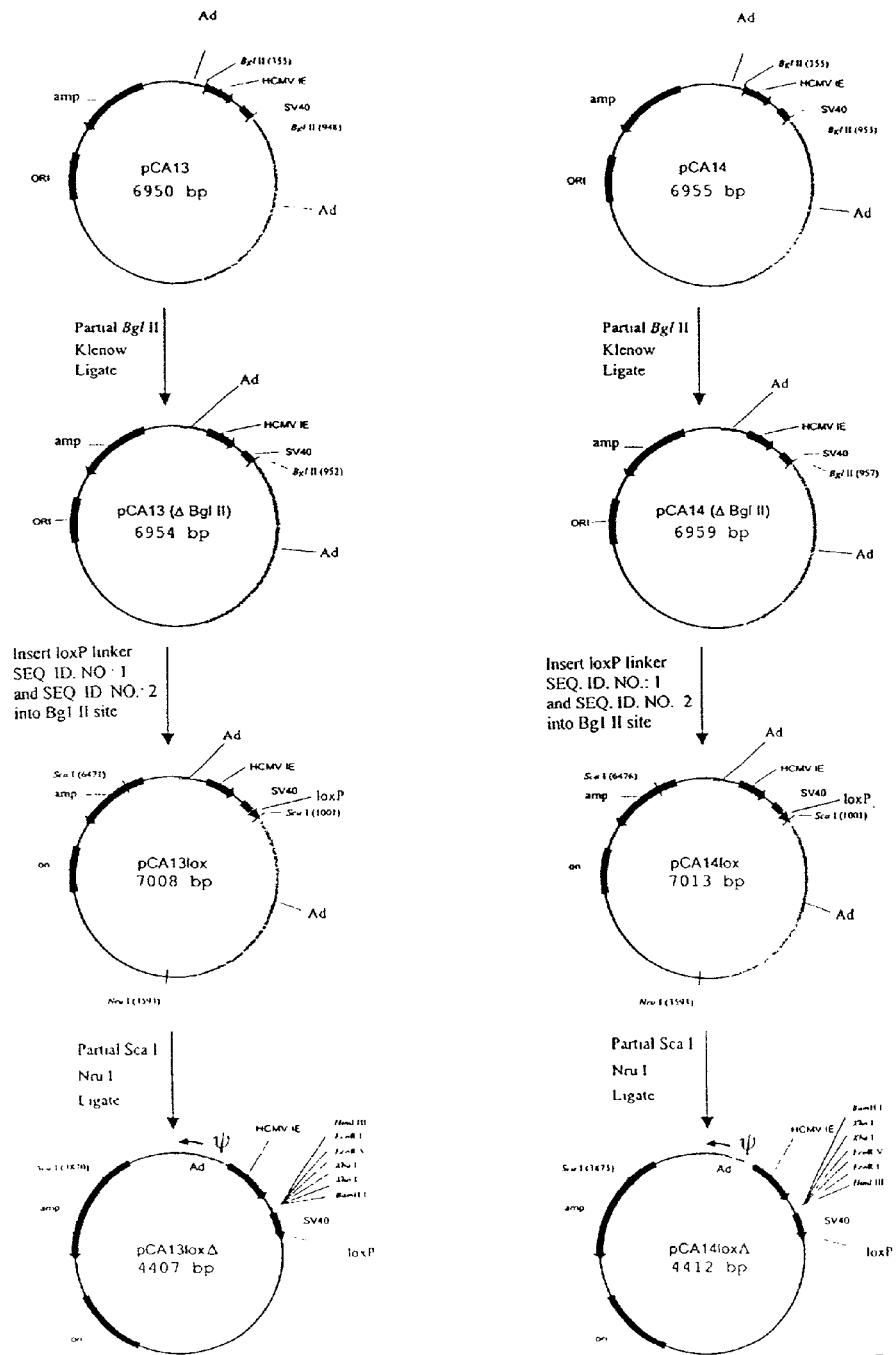
FIG. 7 illustrates construction of HCMV loxP plasmids, pCA13loxΔ and pCA14loxΔ, in which transcription of foreign genes is regulated by the human cytomegalovirus immediate early gene promoter. The plasmids pCA13 (ΔBglII) and pCA14(ΔBglII) were generated by digesting pCA13 and pCA14 partially with BglII, Klenowing and self-ligating. A synthetic loxP oligonucleotide (SEQ ID NO:1 and SEQ ID NO:2; AB3233/3234) was introduced into the unique BglII sites of pCA13(ΔBglII) and pCA14 (ΔBglII) producing pCA13lox and pCA14lox respectively. Ad5 sequences, m.u. 9.8–15.8, were removed from pCA13lox and pCA14lox by cutting each plasmid with NruI and partially digesting each with Seal followed by self ligation.

FIG. 7 illustrates construction of HCMV loxP plasmids in which transcription of foreign genes is regulated by the human cytomegalovirus immediate early gene promoter. The plasmids pCA13 and pCA14 contain the Ad5 genomic sequences from m.u. 0 to 15.8 with E1 sequences between m.u. 1 and 9.8 replaced by the HCMV IE promoter (−299 to +72, relative to the transcription start), a polycloning region and an SV40 polyadenylation signal. (Plasmids pCA13 and pCA14 are available from Microbix Biosystems). The expression cassette in each case is oriented parallel to the direction of E1 transcription (rightwards). The only difference between pCA13 and pCA14 is in the orientation of the multiple cloning region. The plasmids pCA13(ΔBglII) and pCA14(ΔBglII) were generated by digesting pCA13 and pCA14 partially with BglII, Klenowing and self-ligating. A synthetic loxP oligonucleotide (SEQ ID NO:1 and SEQ ID NO:2; AB3233/3234) was introduced into the unique BglII sites of pCA13(ΔBglII) and pCA14(ΔBglII) producing pCA13lox and pCA14lox respectively. Ad5 sequences, m.u. 9.8–15.8, were removed from pCA13lox and pCA14lox by cutting each plasmid with NruI and partially digesting each with ScaI followed by self ligation. The resulting plasmids, pCA13loxΔ and pCA14loxΔ are useful shuttle plasmids for the rescue of first generation Ad vectors by Cre/lox recombination.

Figure 8A:
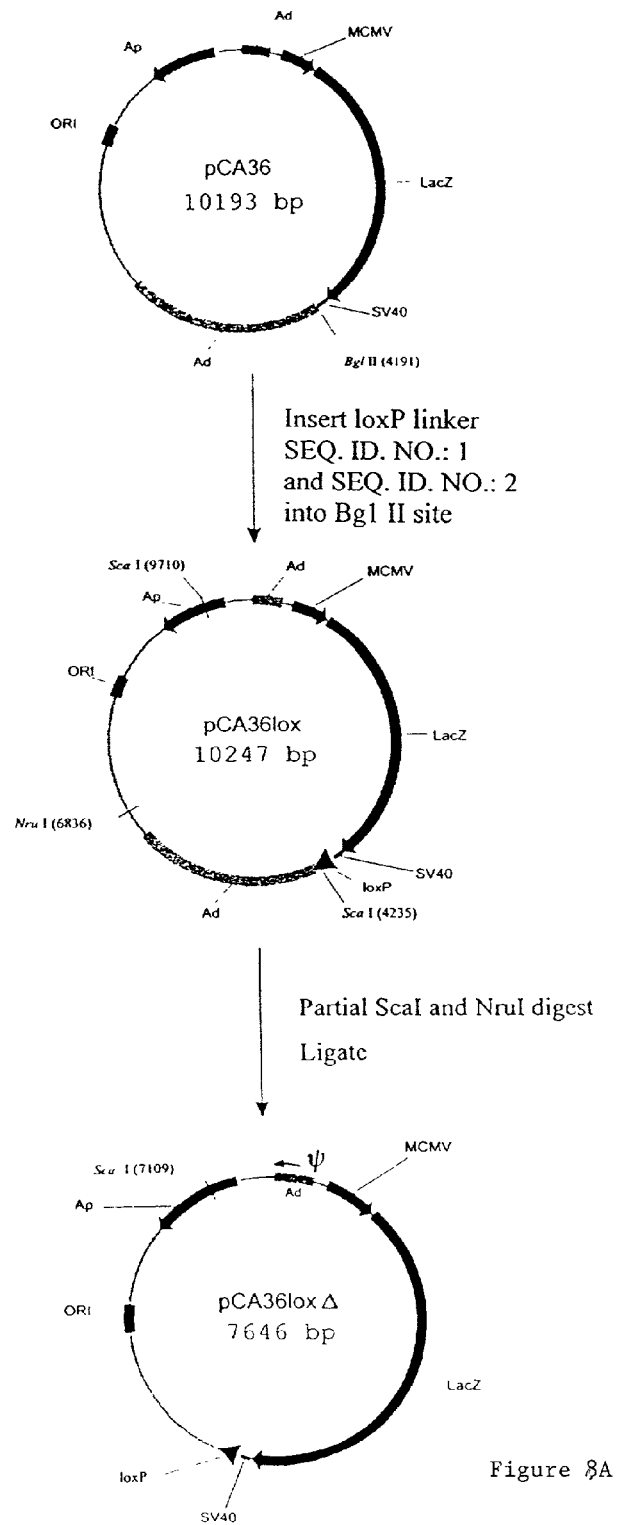
FIG. 8A is a diagrammatic representation of a method for constructing pCA36loxΔ a shuttle plasmid containing the leftmost approximately 340 nt of Ad5, an expression cassette encoding β-galactosidase, and a lox P site for rescue of the LacZ gene into adenovirus vectors. A synthetic loxP site (SEQ ID NO:1 and SEQ ID NO: 2; AB3233/3234) was introduced into the BglII site of pCA36 resulting in pCA36lox. This plasmid was then digested with Nru I and partially digested with Sca I, a 7646 bp fragment was gel purified and self ligated yielding pCA36loxΔ.

FIG. 8A illustrates the construction of a plasmid, pCA36loxΔ, for rescue of the β-galactosidase gene into adenovirus vectors. Naturally, the rescued gene may be any foreign gene, and is not restricted to the use of a marker gene, such as the marker beta-gal gene, which is used herein for illustrative purposes. The plasmid pCA36 contains the β-gal cDNA under control of the short MCMV IE promoter (−491 to +36) followed by an SV40 polyadenylation signal. Plasmid pCA36 was made by inserting the LacZ gene into pMH4 (available from Microbix Biosystems) and is described by Addison, C. L., Hitt, M., Kunsken, D. and Graham, F. L., in "Comparison of the human versus murine cytomegalovirus immediate early gene promoters for transgene expression in adenoviral vectors," J. Gen. Virol. 78: 1653–1661, 1997." A synthetic loxP site (SEQ ID NO:1 and SEQ ID NO:2; AB3233/3234) was introduced into the BglII site of pCA36 resulting in pCA36lox. This plasmid was then digested with Nru I and partially digested with Sca I, a 7646 bp fragment was gel purified and self ligated yielding pCA36loxΔ. This plasmid contains Ad sequences from m.u. 0–1, and not only has the deletion of E1 sequences present in the parental plasmids pCA36 and pCA36lox, but additionally is deleted of Ad5 sequences from m.u.9.8–15.8.

EXAMPLE 6

Demonstration of Enhanced Efficiency of Site-specific Recombination in Comparison with Homologous Recombination In a third embodiment of the invention, two plasmids containing loxP or other recombinase recognition sites are cotransfected into 293Cre or other appropriate cells (expressing an appropriate recombinase, Cre for purposes of this example). The Cre enzyme catalyses site-specific recombination between said lox P sites present in each vector. As illustrated in FIG. 1, it will be readily seen by one skilled in the art that Cre-mediated recombination between said lox P sites generates a viable virus by joining pBHG sequences to a DNA segment containing ψ and ITR sequences. Furthermore, by virtue of the design and construction of the pBHG derivative and the shuttle plasmid, the resulting viral vector contains the expression cassette located to the left of the lox P site in said shuttle plasmid, thereby providing a simple and efficient means for isolating viral vectors containing foreign DNA insertions and expression cassettes for synthesis of proteins from foreign genes.

To test and demonstrate the validity of the approaches outlined above and to determine the degree of improvement in efficiency of vector isolation compared to known methods, a number of experiments were conducted in which a vector carrying a LacZ expression cassette inserted near the left end of the Ad genome was constructed. The efficiency of Cre/lox mediated recombination was compared with that of homologous recombination, by measuring the numbers of virus plaques obtained from cotransfections of 293 cells versus the numbers obtained following cotransfections of 293Cre4 cells (see, for example, U.S. patent application Ser. No. 08/473,168, filed Jun. 7, 1995; see also WO96/40955, hereby incorporated by reference).

The results shown in Table 1 indicate that Cre/lox mediated recombination (cotransfections of 293Cre4 cells with plasmids that both contain lox sites) was approximately 35-fold more efficient than homologous recombination (cotransfections of 293 cells or cotransfections of 293Cre4 cells with plasmids that do not both contain lox sites). A 35-fold increase represents a very significant and unexpectedly high improvement over efficiencies of vector rescue when virus isolation is dependent on homologous recombination. Coupled with the fact that the only infectious virus present in the transfected cell preparation are recombinants, rather than contaminating starting virus, the efficiency, cleanliness and convenience of this method in comparison to known methods represent significant advances in the art. Thus, with this new method it will be possible to reduce the amount of plasmid DNA used in cotransfections and reduce the number of dishes of 293 (293Cre) cells needed in cotransfections for rescue of viral vectors. It will also aid in the rescue of constructs which, for unknown reasons, might be otherwise difficult to rescue (e.g. rescue of vectors containing large foreign DNA inserts in E1 is often inefficient for reasons that are not known).

To confirm that the enhanced efficiency of plaque formation following cotransfection of 293Cre cells with pCA36+ pBHG10lox was due to Cre-lox dependent recombination (versus, for example, enhanced efficiency of homologous recombination) we constructed a derivative of pCA36lox, named pCA36loxΔ (see FIG. 8A), from which overlapping Ad sequences to the right of the lox site had been removed, thus eliminating any possibility of homologous recombination. This new shuttle plasmid was then tested for ability to generate vectors in a second experiment in which 293 or 293Cre cells were cotransfected with this plasmid or with pCA36 or pCA36lox for comparison along with pBHG10lox. It can be seen from the results shown in Table 2 that pCA36loxΔ only generated viral plaques following cotransfection of 293Cre cells with pBHG10lox. In contrast pCA36 or pCA36lox were able to generate small numbers of plaques on 293 cells. However, again, the efficiency was markedly enhanced if 293Cre cells were cotransfected with pCA361lox and pBHG10lox. Thus the use of Cre-lox recombination results in a surprisingly efficient system for rescue of foreign DNA into Adenovirus vectors.

To confirm that transfection of 293Cre cells with pCA36lox (a lacZ-containing shuttle plasmid with a loxP site located between the expression cassette and the pIX coding sequence as illustrated in FIG. 8) and pBHG10lox resulted in viruses containing the desired insert of foreign DNA, 26 recombinant plaques were isolated, expanded and analysed for expression of LacZ. All 26 (100%) were positive for β-galactosidase expression. Furthermore, analysis of the structure of the viruses confirmed that all 26 had the expected DNA structure illustrated in FIG. 1. Further confirmation of the efficiency and specificity of the Cre/lox system for rescue of expression cassettes was obtained through analysis of 6 plaque isolates obtained by cotransfection of 293Cre cells with pCA36loxΔ and pBHG10lox (Table 2). All 6 plaque isolates expressed β-galactosidase and all 6 had the expected DNA structure illustrated in FIG. 1. Because 100% of recombinant viruses produced by cotransfection of 293 Cre cells with plasmids containing appropriately engineered lox sites have the correct structure and express the transgene, (β-galactosidase in these examples), it will be appreciated by those skilled in the art that one could readily produce recombinant viruses carrying other foreign DNA inserts by constructing shuttle plasmids derived from the plasmids shown in FIGS. 5, 6 and 7 or similar plasmids, and cotransfecting said modified shuttle plasmids into 293Cre or like cells, along with pBHG1010× or similar pBHG plasmids containing a lox site near the end of E1. It will be further appreciated by those skilled in the art that because of the high-efficiency of rescue with this approach, only small numbers of 293Cre cultures and small amounts of DNA need be used to obtain the desired recombinant viruses. Furthermore, because only the desired recombinant viruses are obtained from said cotransfections, it would not be essential to plaque purify and analyse viral progeny obtained according to the method of this invention. In addition, after the initial isolation of the recombinant viruses from 293 Cre cells, said viruses can be propagated in host cells such as 293, 911 or PERC-6 cells or the like which do not express recombinase.

EXAMPLE 7

Site-specific Shuttle Plasmid-Virus Recombination

Hardy et al., J. Virol. 1997, March: 71(3):1842–1849, and see also WO97/32481 disclosed a method whereby an infectious DNA vector was used in combination with a plasmid in combination with lox-Cre recombination to generate recombinant adenoviruses. However, according to that method, residual infectious starter virus remain in the recombinant virus preparation, requiring repeated passage of the preparation in a Cre expressing cell to eliminate this background. An advancement to such techniques is provided herein by combination of Cre-lox recombination and use of adenoviral DNA bound to the adenoviral terminal protein (TP). The result of this combination is high-efficiency infection combined with site-specific recombination.

Figure 8B:
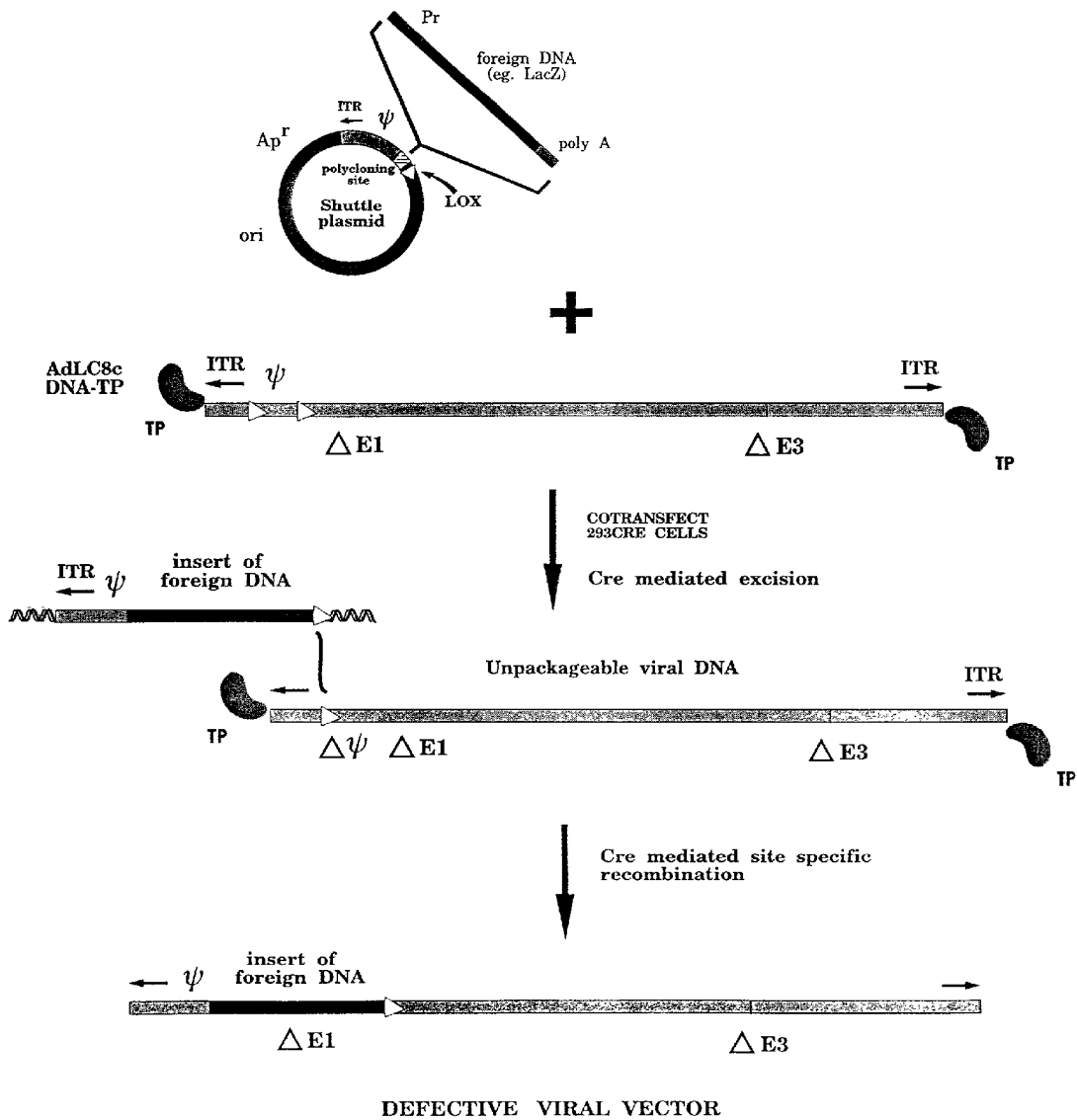
FIG. 8B is a diagrammatic representation of a means to isolate adenoviral vectors containing an expression cassette by cotransfection of 293Cre cells with (a) AdLC8c DNA-TP complex having covalently bound terminal protein (TP) linked to the 5' ends of Adenoviral DNA and (b) a shuttle plasmid containing an expression cassette and a lox P site. Cre-mediated excision of the floxed packaging signal of AdLC8c renders the AdLC8c genome defective for packaging. A second Cre-mediated recombination event between the lox sites in the shuttle plasmid and the AdLC8c genome results in a vector with a packaging signal, the foreign DNA insert, and a single lox site.
Figure 8C:
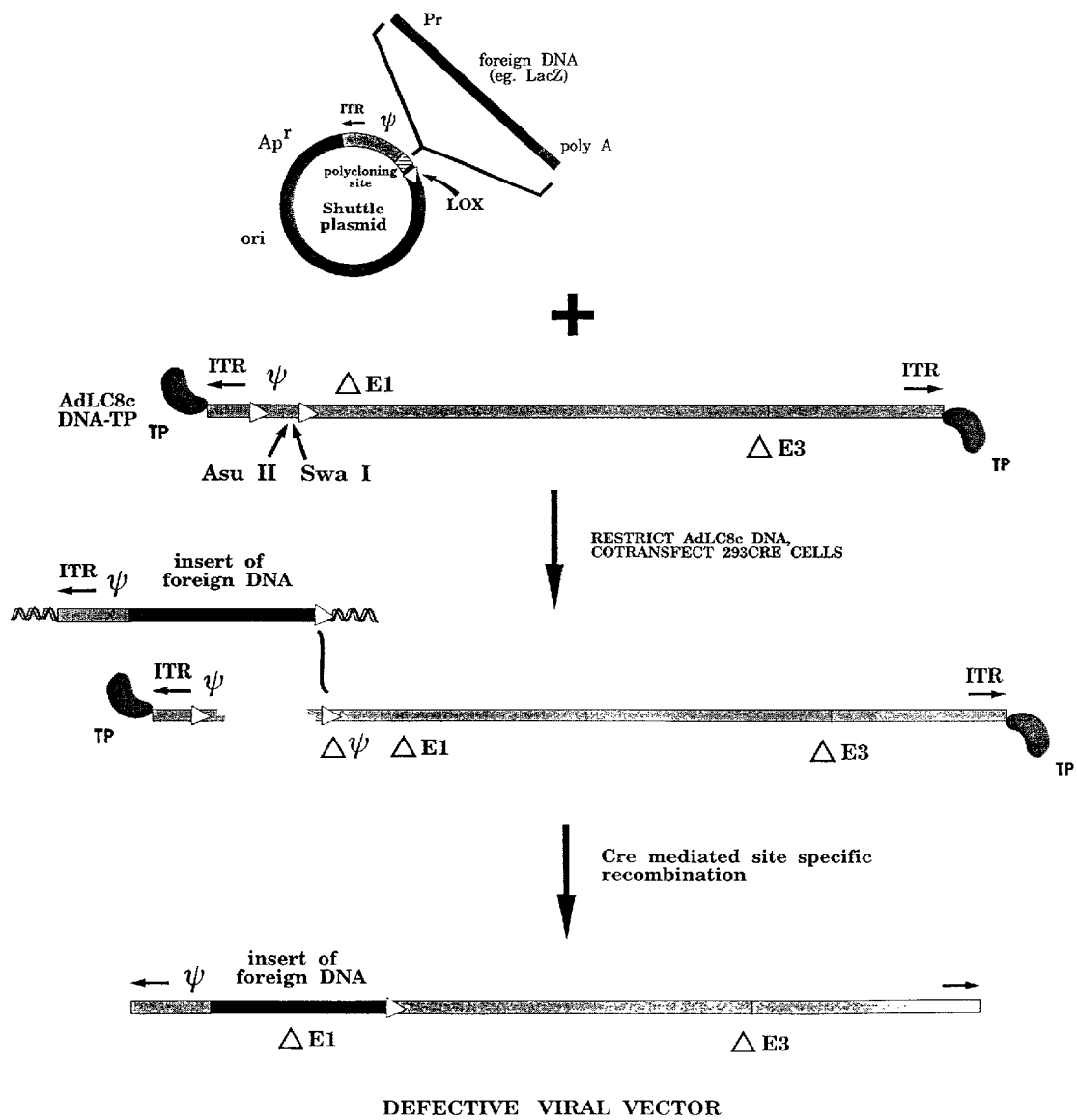
FIG. 8C is a diagrammatic representation of a means to isolate adenoviral vectors containing an expression cassette by cotransfection of 293Cre cells with restricted AdLC8c DNA-TP and a shuttle plasmid containing an expression cassette and a lox P site. AdLC8c DNA-TP is cleaved with an endonuclease such as Asu II or Swa I that recognize unique restriction enzyme sites between the lox sites flanking ψ. Cleavage of viral DNA with restriction enzymes prior to cotransfection reduces the infectivity of parental virus DNA and when combined with the high-efficiency of Cre-mediated recombination results in high-efficiency of vector isolation in cotransfected 293Cre cells as illustrated. Rejoining of parental DNA fragments and generation of infectious parental virus rather than the desired vector is avoided because of the action of Cre on the floxed packaging signal in AdLC8c. However, when the viral DNA-TP complex is cut with a restriction enzyme as illustrated, the level of Cre-mediated recombination is sufficiently high that most, if not all, progeny viruses result from recombination between the shuttle plasmid and the large DNA-TP fragment. Therefore, the left-most lox site of AdLC8c and equivalent vectors is not essential.

The use of a two plasmid system for isolation of viral vectors or modified viruses is not meant to be limiting. From the instant disclosure, it will be appreciated by those skilled in the art that one could use, as one component of the system, viral DNA from a modified virus whose genome contains lox P sites at useful positions. An excellent example, not meant to be limiting, is use of AdLC8, AdLC8c or AdLC8cluc described by Parks, R. J., Chen, L., Anton, M., Sankar, U., Rudnicki, M. A. and Graham, F. L., in "A new helper-dependent adenovirus vector system: removal of helper virus by Cre-mediated excision of the viral packaging signal," Proc. Natl. Acad. Sci. U.S. 93: 13565–13570, 1996. These viruses contain a "floxed" packaging signal, which is excised following virus infection of 293Cre cells. Therefore, cotransfection of 293Cre cells with viral DNA extracted from AdLC8, AdLC8c or AdLC8cluc in such a way as to retain the covalent linkage to TP, according to methods taught by Sharp et al., "The infectivity of adenovirus 5 DNA-protein complex," Virology, 1976 December: 75(2): 442–456; Chinnadurai, et al., "Enhanced infectivity of adenovirus type 2 DNA and a DNA-protein complex," J. Virol. 1978 April: 26(1):195–199, and a shuttle plasmid such as that illustrated in FIG. 5, 6, 7 or 8A results in Cre-mediated recombination to generate a new vector containing the sequences derived from the shuttle plasmid, spanning the region from the ITR and packaging signal of the shuttle across the optional polycloning site or optional expression cassette to the lox P site of said shuttle plasmid. For example, not meant to be limiting, as illustrated in FIG. 8B, using a lacZ-encoding plasmid, similar to that shown in FIG. 8A, and AdLC8c DNA-TP, one skilled in the art could readily isolate the desired recombinant virus containing lacZ or other foreign genes by cotransfection of 293Cre cells with DNA extracted from AdLC8c-TP and said Lac Z-encoding plasmid. Optionally, as illustrated in FIG. 8C, one could cotransfect 293 Cre cells with restriction endonuclease treated AdLC8c DNA-TP and a shuttle plasmid selected from the set of plasmids illustrated in FIGS. 5, 6, 7 and 8A to produce infectious virus by Cre-mediated recombination. The viral DNA extracted from AdLC8c according to this method retains the terminal protein which has been shown to increase the efficiency of transduction of recipient cells with said DNA (Sharp P A, Moore C, Haverty J L, "The infectivity of adenovirus 5 DNA-protein complex," Virology 1976 December; 75(2):442–456). It will be apparent to those skilled in the art that the left most lox site is not needed and may optionally be deleted if AdLC8cDNA-TP is to be cut with restriction enzymes prior cotransfection. Furthermore, optionally, after restriction enzyme digestion, the large right end fragment of AdLC8cDNA-TP could be purified prior to cotransfection.

Figure 8D:
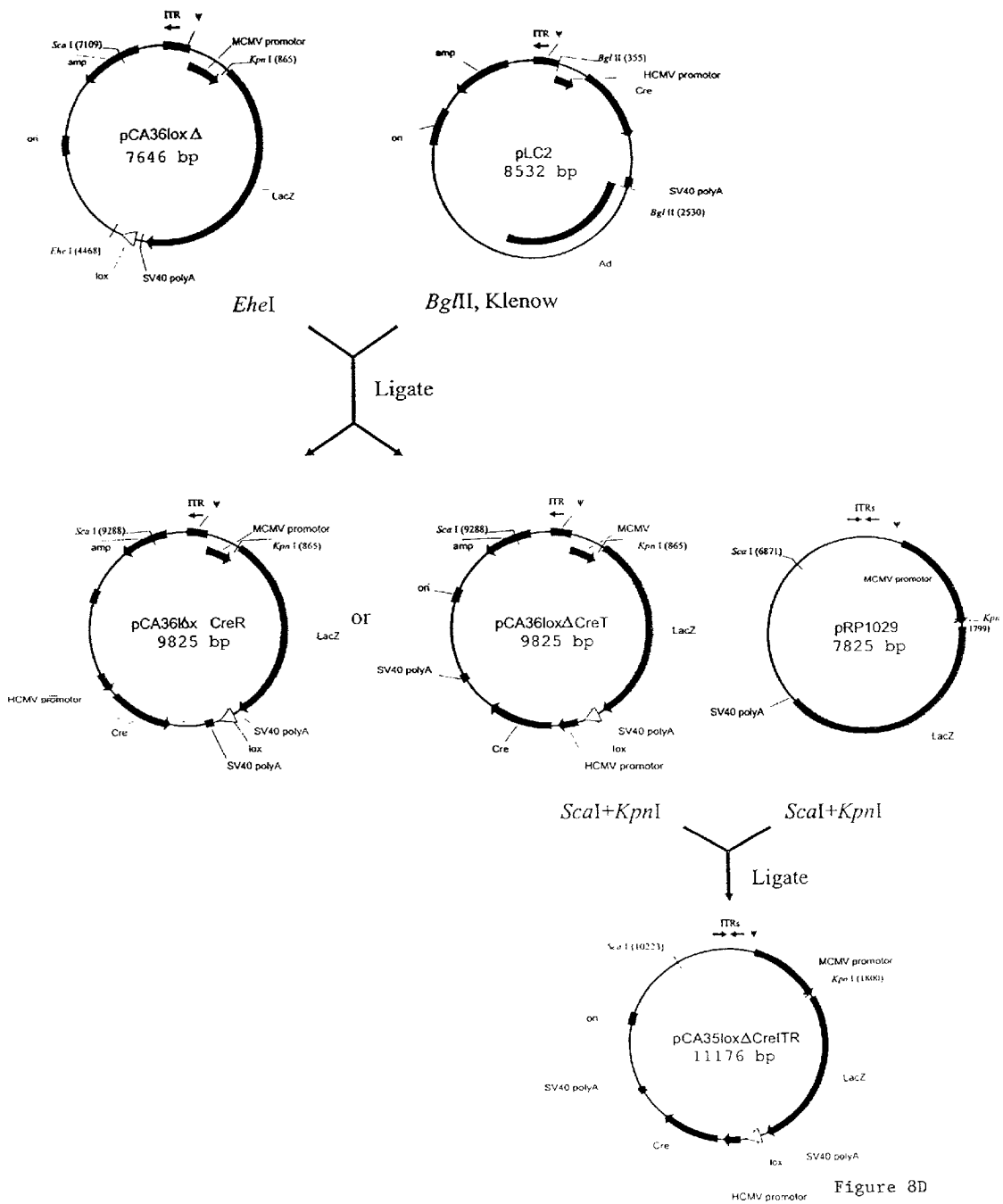
FIG. 8D is a diagrammatic representation of a method for constructing shuttle plasmids expressing Cre. The Cre expression cassette was obtained from the plasmid pLC2 (Chen, L., Anton, M. and Graham, F. L., "Production and characterization of human 293 cell lines expressing the site-specific recombinase Cre," Somat. Cell and Molec. Genet. 22:477–488, 1996), as a 2175 bp BglII fragment which was end-modified with Klenow DNA polymerase and inserted into the EheI site of pCA36loxΔ to generate pCA36loxΔCreR and pCA36loxΔCreT. The plasmid pCA36loxΔCreITR was constructed by replacing the 1402 bp ScaI/KpnI fragment in pCA36loxΔCreT with the 2753 bp ScaI/KpnI fragment from the plasmid pRP1029. Plasmid pCA36loxΔCreITR contains ITR junctions which are known to be functionally capable of generating replicating linear Ad DNA molecules (Graham, F. L., "Covalently closed circles of human adenovirus DNA are infections," The EMBO J. 3, 2917–2922, 1984).

FIG. 8D is a diagrammatic representation of a method for constructing shuttle plasmids expressing Cre. The Cre expression cassette was obtained from the plasmid pLC2 (Chen, L., Anton, M. and Graham, F. L., "Production and characterization of human 293 cell lines expressing the site-specific recombinase Cre," Somat. Cell and Molec. Genet. 22:477–488, 1996), as a 2175 bp BglII fragment which was end-modified with Klenow DNA polymerase and inserted into the EheI site of pCA36loxΔ to generate pCA36loxΔCreR and pCA36loxΔCreT. The plasmid pCA36loxΔCreITR was constructed by replacing the 1402 bp ScaI/KpnI fragment in pCA36loxΔCreT with the 2753 bp ScaI/KpnI fragment from the plasmid pRP 1029. Plasmid pCA36loxΔCreITR contains ITR junctions which are known to be functionally capable of generating replicating linear Ad DNA molecules (Graham, F. L., "Covalently closed circles of human adenovirus DNA are infections," The EMBO J. 3, 2917–2922, 1984).

Figure 8E:
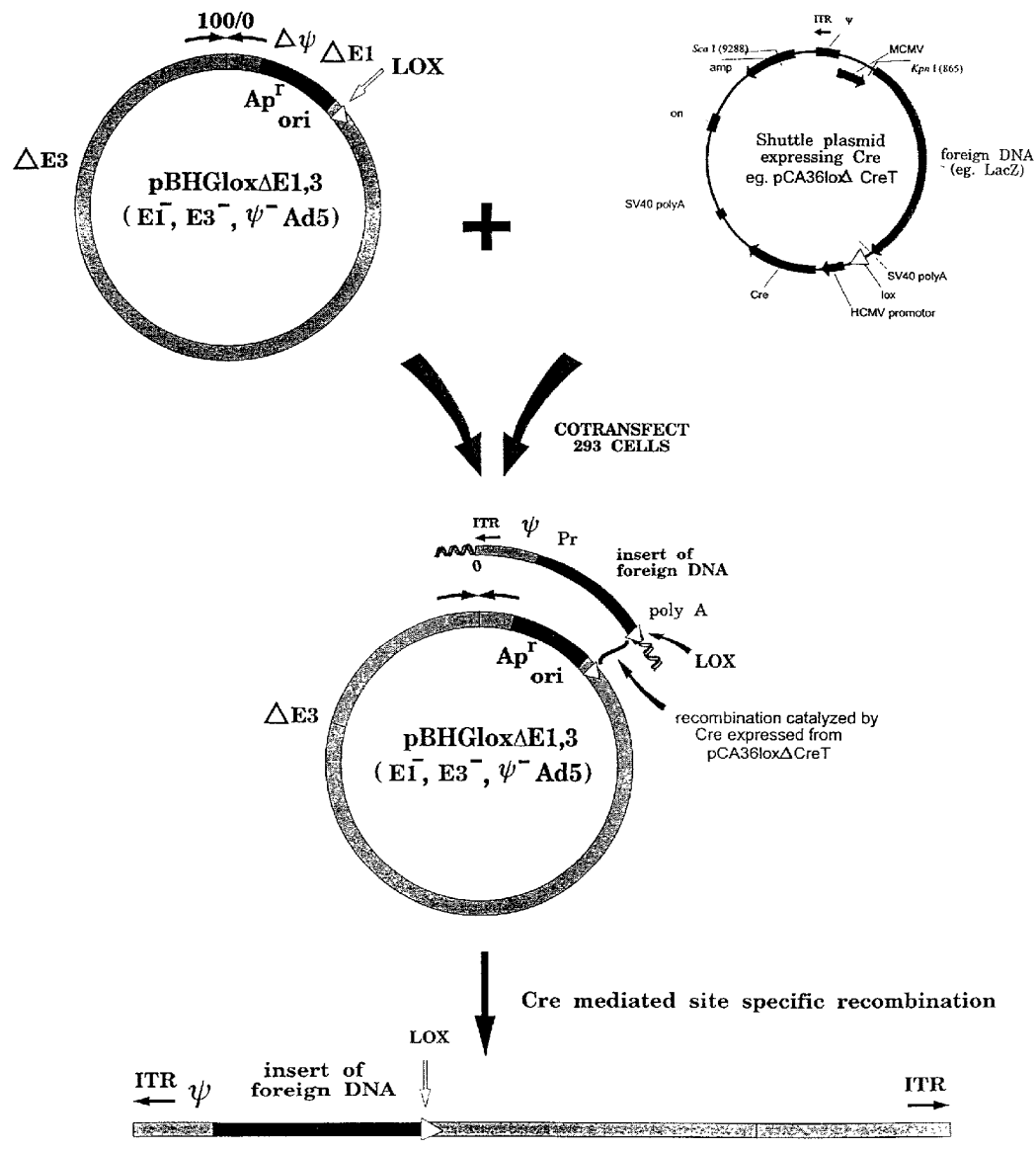
FIG. 8E provides a schematic representation of a cotransfection experiment wherein a pBHG10lox plasmid and a "Lox" shuttle plasmid expressing Cre are introduced into 293 cells in order to generate Ad expression vectors, without having to use cells which stably express Cre. This technique is applicable to any cell type suitable for Ad vector generation, including but not limited to 293 cells, and PER-C6 cells (Fallaux et al., Hum. Gene Ther. 1998, September 1; 9(13): 1909–17), 911 cells (Fallaux et al., Hum. Gene Ther. 1996 January 20; 7(2):215–222), or other cells. A shuttle plasmid such as pCA36loxΔCreITRof

FIG. 8E provides a schematic representation of a cotransfection experiment wherein a pBHG10lox plasmid and a "Lox" shuttle plasmid expressing Cre are introduced into 293 cells in order to generate Ad expression vectors, without having to use cells which stably express Cre. This technique is applicable to any cell type suitable for Ad vector generation, including but not limited to 293 cells, and PER-C6 cells (Fallaux et al., Hum. Gene Ther. 1998, September 1; 9(13): 1909–17), 911 cells (Fallaux et al., Hum. Gene Ther. 1996 January 20; 7(2):215–222), or other cells. A shuttle plasmid such as pCA36loxΔCreITR of FIG. 8D is also suitable for generation of an Ad vector. The efficiency of Ad vector rescue by cotransfection with pBHGlox and various shuttle plasmids is summarized in Tables 3 and 4. It can be seen from the results in Table 4 that inclusion of an ITR junction in the shuttle plasmid increases the efficiency of rescue significantly. Thus, provision of an ITR junction is a preferred, although not required, embodiment.

Insertion of an expression cassette encoding Cre recombinase in the shuttle plasmid is not meant to be limiting as one skilled in the art will appreciate that one could also insert a Cre cassette in the larger plasmid, pBHG10lox. An example, not meant to be limiting, is diagrammed in FIG. 8F, which illustrates the construction of such a plasmid. It will be appreciated that the Cre expression cassette could be carried by either of the two plasmids used in the cotransfections such as that illustrated in FIG. 1, or by both of them, so that Cre is supplied at adequate levels in cotransfected 293 cells to catalyse efficient recombination between the lox sites of the cotransfected plasmids. Thus mention of the use of 293Cre cells or like cells expressing Cre recombinase is not meant to be limiting.

Figure 8F:
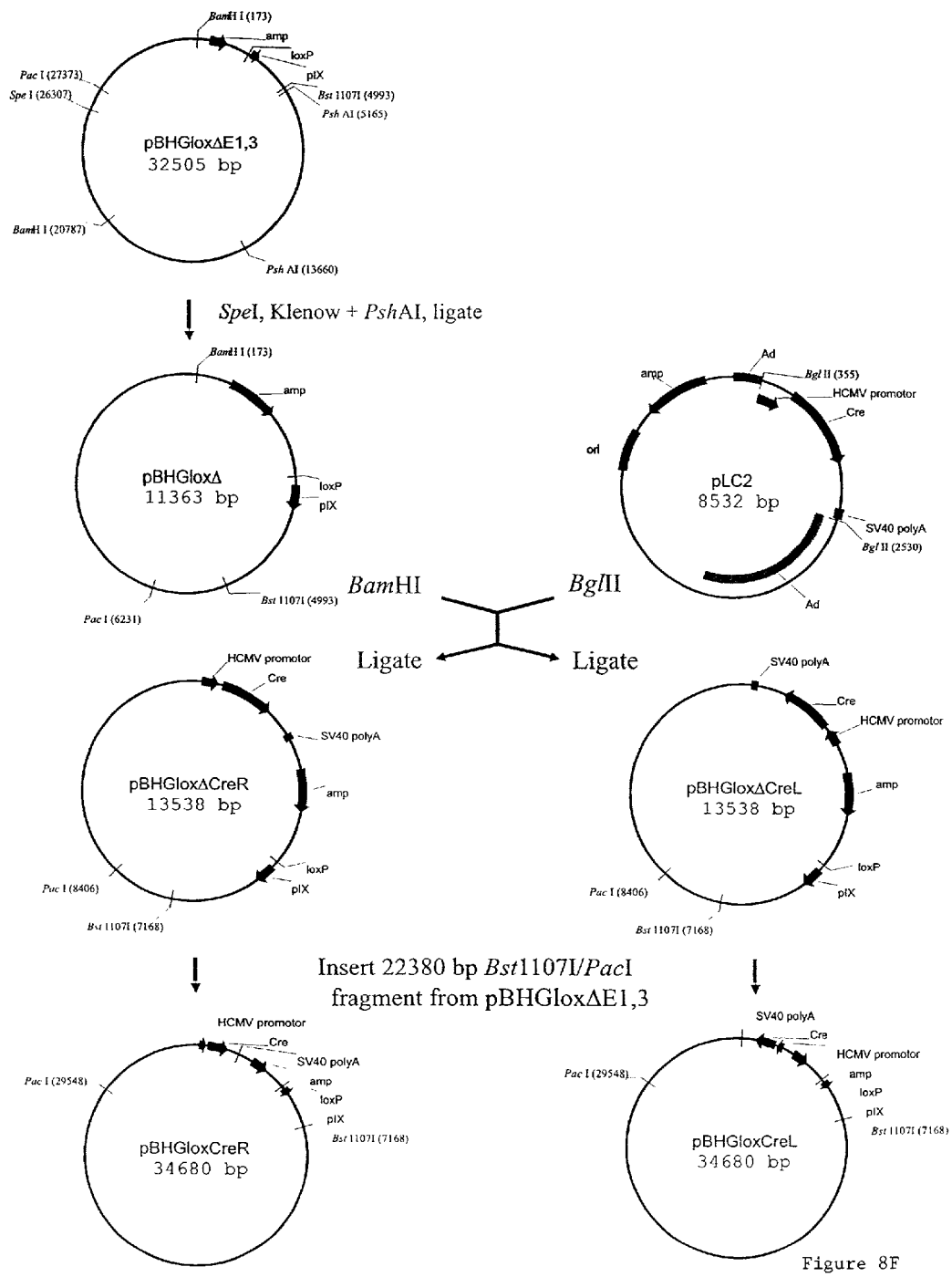
FIG. 8F. Demonstrates the construction of an Ad genomic plasmid encoding Cre. The plasmid pBHG10loxΔ was constructed by collapsing pBHG10lox with SpeI and PshAI. The Cre expression cassette, taken from the plasmid pLC2 as a 2175 bp BglII fragment, was inserted into the BamHI site of pBHG10loxΔ to generate pBHG10loxΔCreR and pBHG10loxΔCreL. The 1238 bp Bst1107I/PacI fragment from pBHG10loxΔCreR and pBHG10loxΔCreL was replaced with the 22380 bp Bst1107I/PacI fragment from pBHG10lox to generate pBHG10loxCreR and pBHG10loxCreL, respectively.

FIG. 8F demonstrates the construction of an Ad genomic plasmid encoding Cre. The plasmid pBHG10loxΔ was constructed by collapsing pBHG10lox with SpeI and PshAI. The Cre expression cassette, taken from the plasmid pLC2 as a 2175 bp BglII fragment, was inserted into the BamHI site of pBHG10loxΔ to generate pBHG10loxΔCreR and pBHG10loxΔCreT. The 1238 bp Bst1107I/PacI fragment from pBHG10loxΔCreR and pBHG10loxΔCreT was replaced with the 22380 bp Bst1107I/PacI fragment from pBHG10lox to generate pBHG10loxCreR and pBHG10loxCreT, respectively.

EXAMPLE 8

Rescue of Foreign DNA and Mutations into any Desired Location in the Adenoviral Genome The above examples illustrating rescue of foreign DNA into the E1 region of Ad vectors are not meant to be limiting. It will be appreciated by those skilled in the art that one could equally follow the instructions outlined above to construct similar plasmids for the rescue of insertions or mutations or deletions into E1 or other regions of the viral genome. For example, not meant to be limiting, one could construct a series of analogous plasmids suitable for rescue of fibre mutations into the viral genome or for rescue of foreign DNA inserts in the E3 region of the viral genome into infectious virus. An example, not meant to be limiting, is provided in FIG. 9A, which is a diagrammatic representation of a method for rescuing fibre mutations into infectious virus using Cre-loxP recombination. Cotransfection of 293Cre cells with pFG173lox and a shuttle plasmid containing a loxP site 5' of the fibre gene results in site-specific recombination between the lox sites and rescue into infectious virus of the adenoviral sequences of the shuttle, which sequences may optionally contain a mutated fibre gene.

Figure 9A:
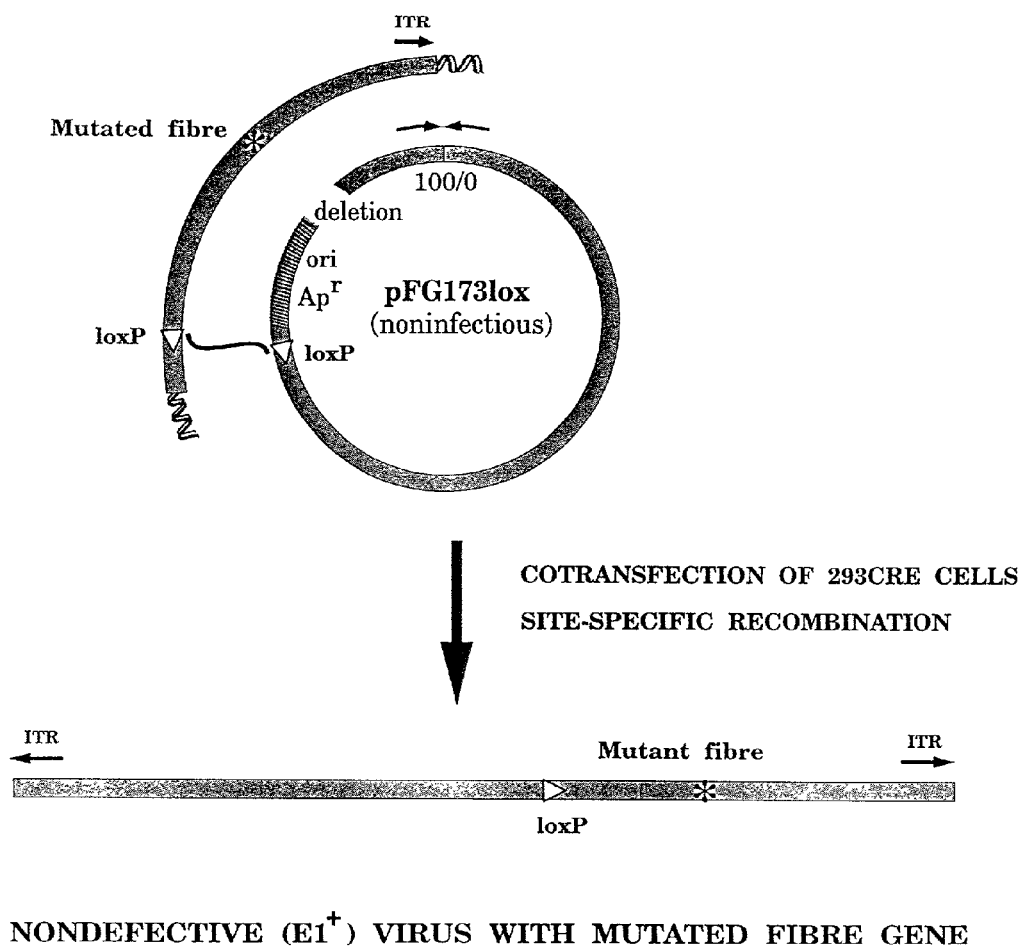
FIG. 9A is a diagrammatic representation of a method for rescuing fibre mutations into infectious virus using Cre-lox recombination. Plasmid pFG173lox is derived from pFG173 which is a bacterial plasmid containing most of the Ad5 genome but from which sequences have been deleted (represented by "deletion" in the diagram) that render the plasmid noninfectious. The sequences are substituted with bacterial DNA containing an antibiotic resistance gene and a bacterial plasmid origin of DNA replication. A lox site upstream (leftward in the conventional map of the Ad genome) of the deletion/substitution is inserted in the plasmid for Cre-mediated recombination with a similar lox site in a shuttle plasmid containing the right region of the viral genome from approximately 85 mu to approximately 100 mu and including most or all of the right ITR. Recombination as illustrated generates an infectious virus containing sequences representing the left approximately 78 mu of the Ad genome derived from pFG173lox and sequences from approximately 85–100 mu derived from the shuttle plasmid.
Figure 9B:
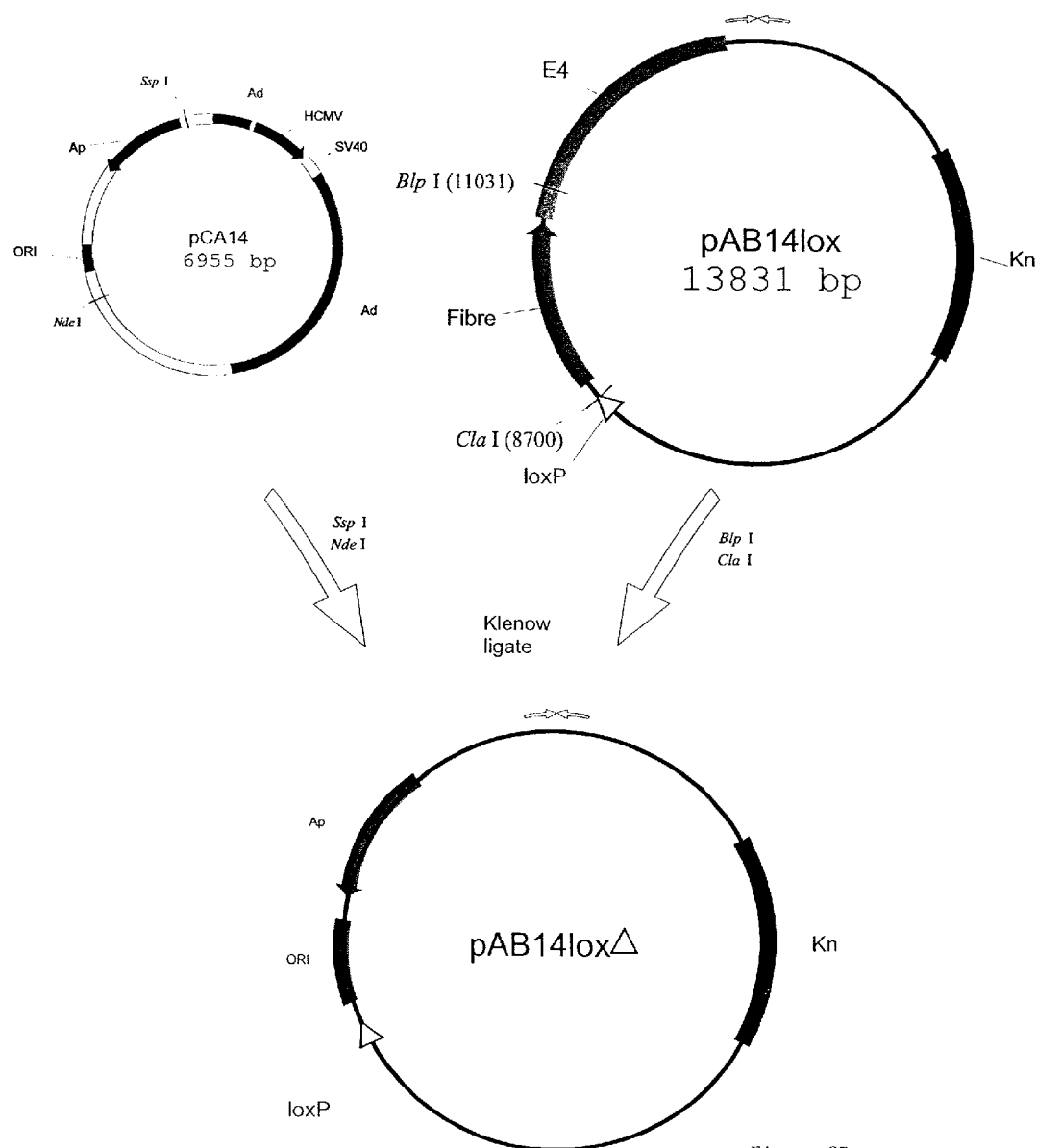
FIG. 9B is a diagrammatic representation of a method for constructing a plasmid containing a lox site and ampicillin resistance gene substituting for the fibre gene. Starting with pAB14lox whose construction is described in FIG. 14, the DNA sequences between the Cla I site and the Blp I site containing fibre are substituted with a DNA segment containing the ampicillin resistance gene and a plasmid origin of DNA replication. The NdeI to Ssp I DNA fragment from pCA14 (Microbix Biosystems) containing ampicillin resistance gene and plasmid origin of DNA replication is treated with Klenow DNA polymerase and ligated with a similarly treated Blp I to ClaI fragment of pAB14lox to generate the ampicillin and kanamycin doubly resistant, fibre gene deleted, pAB14loxΔ.

FIG. 9B is a diagrammatic representation of a method for constructing a plasmid containing a lox site and ampicillin resistance gene substituting for the fibre gene. Starting with a plasmid such as pAB14lox, construction of which is described in FIG. 14, the DNA sequences between the Cla I site and the Blp I site containing fibre are substituted with a DNA segment containing the ampicillin resistance gene and a plasmid origin of DNA replication (which may optionally be obtained by restriction endonuclease digestion of an ampicillin resistant plasmid such as pCA14 (Microbix Biosystems)).

FIG. 9C is a diagrammatic representation of a method for combining the plasmid of FIG. 9B with pFG173 to produce pFG173lox for rescuing fibre mutations into infectious virus using Cre-lox recombination. The plasmid pAB14loxΔ illustrated in FIG. 9B comprises Ad sequences 3' of fibre to mu 100. The plasmid additionally contains viral DNA sequences 5' of fibre, but has all of the fibre coding sequences deleted and substituted with a plasmid origin of DNA replication and an antibiotic resistance gene, such as for ampicillin resistance. Sequences from pAB14loxΔ can be recombined with pFG173 (Microbix Biosystems) by homologous recombination in *E. coli* (Chartier C, Degryse E, Gantzer M, Dieterle A, Pavirani A, Mehtali M., "Efficient generation of recombinant adenovirus vectors by homologous recombination in *Escherichia coli*," J Virol 1996 July; 70(7):4805–4810). The resulting plasmid, pFG173lox, has a deletion of sequences comprising all of the fibre gene or optionally part of the fibre gene or optionally all or part of E4 or optionally a deletion of all or part of both fibre and E4, and is consequently unable to produce infectious virus following transfection of cells. However, on recombination with a plasmid such as pFG23dX1lox or a similar plasmid, infectious virus can be readily generated, as illustrated in FIG. 9A. Said recombination can be efficiently catalysed by Cre recombinase, if pFG173lox and pFG23dX1lox are cotransfected into 293Cre cells or similar host cells expressing Cre recombinase.

Construction of plasmids suitable for rescue of fibre or E4 gene mutations or deletions or substitutions can be readily accomplished by one skilled in the art based on the present disclosure. An example, not meant to be limiting, of the construction of one such plasmid is illustrated in FIG. 10, which is a diagrammatic representation of a plasmid containing the right approximately 40% of the virus genome, wherein a lox P site has been inserted near the 5' end of the fibre gene. PFG23dX1 contains the right approximately 40% of the Ad 5 genome from nt 21563 (mu 60) to approximately the right end of the genome (mu 100) cloned into the BamH I site of pBR322 and additionally has a deletion of Ad5 sequences from 28593 to 30471, comprising most of E3 (Haj-Ahmad, Y. and Graham, F. L., "Development of a helper independent human adenovirus vector and its use in the transfer of the Herpes Simplex Virus thymidine kinase gene," J. Virol. 57, 267–274, 1986). PFG23dX1 was digested with XbaI and a synthetic oligonucleotide (SEQ ID NO:5 and SEQ ID NO:6; AB6920/AB6921, FIG. 3) containing a loxP site was inserted. The resulting plasmid, pFG23dX1lox, can be used for generation of infectious virus by cotransfection of 293Cre cells with a plasmid such as pFG173lox (FIG. 9A). Optionally, viral genes, such as those encoding fibre or genes of E4 can be mutated in pFG23dX1lox and the resulting mutations rescued into virus. Because Ad sequences 5' of the lox site (counterclockwise in the diagram) are not necessary when Cre-mediated site specific, rather than homologous, recombination is used to generate infectious virus, viral sequences between a unique Bst 11071 site and a BsiW1 site immediately 5' of the lox P site were deleted to generate pFG23dX1loxc.

One skilled in the art would appreciate, based on the instant disclosure, that just as Cre recombinase may be provided by inserting a Cre expression cassette in one or another or both of the cotransfecting plasmids to facilitate recombination between plasmids designed to rescue mutations or insertions in E1, similarly, one may insert said expression cassette into either or both of the plasmids to be recombined as diagrammed in FIG. 9A so that site specific recombination can be achieved in host cells that do not express the recombinase constitutively. In a preferred embodiment, the shuttle plasmid thus modified would be further modified to contain a junction of ITRs as the results shown in Table 4 indicate that said junction results in a significant improvement in efficiency of virus production. As in the examples illustrated in FIGS. 8D and 8F, said plasmids would most often be designed so that the Cre expression cassette would not be rescued into the infectious viral genomes that are thus generated.

Examples illustrating rescue of mutations into infectious virus are not meant to be limiting as one killed in the art could readily appreciate that the methods described herein are equally employed to rescue insertions of foreign DNA into the viral genome. An example of a suitable plasmid that is readily constructed is pFG23dX1LacZlox. FIG. 11 is a diagrammatic representation of said plasmid wherein a foreign DNA, such as a gene encoding bacterial lacZ, is inserted between the lox P site and the fibre gene. In this example, not meant to be limiting, an expression cassette encoding β-galactosidase is inserted into the Cla I site adjacent to the loxP of pFG23dX1 lox (FIG. 10) for subsequent rescue into infectious virus by the method illustrated in FIG. 9A. It will be appreciated by those skilled in the art that other foreign DNAs could readily be rescued into infectious virus genomes by the methods illustrated above. Said foreign DNA segment could be a separate expression cassette or a fusion of sequences encoding peptide sequences to sequences encoding fibre, said peptide sequences representing, for example, a ligand to a cell surface receptor such that the rescued virus expressing a modified fibre would have novel and useful cell attachment properties. This example is not meant to be limiting as it will be appreciated by one skilled in the art that lox P sites can readily be introduced into other positions of the viral DNA for substitution of other virion genes with mutated counterparts.

These examples are not meant to be limiting as one could construct a plasmid similar to pFG173lox from which other viral genes have been deleted such as, for example, those of E1 such that the resulting viruses generated by Cre-mediated recombination are E1 deleted viruses.

EXAMPLE 9

Use of Engineered Adenoviruses Produced According to this Invention

The use of the two plasmid system in combination with Cre-mediated site-specific recombination is not meant to be limiting as one skilled in the art will readily appreciate that, as taught for the generation of viruses carrying E1 mutations, deletions and insertions, one could employ viral DNA isolated from suitably engineered viruses for the manipulation of the viral genome by Cre-mediated recombination. For example, as illustrated in FIGS. 12 and 13, 293Cre cells are cotransfected with DNA extracted from a virus containing a floxed fibre gene in such a way as to retain either or both terminal proteins, TP. Optionally the DNA is digested with restriction enzymes that cut sequences between the lox sites prior to cotransfections. It will be apparent to those skilled in the art, based on the instant disclosure, that the right most lox site is not needed and may optionally be deleted or omitted if DNA-TP is to be cut with restriction enzymes prior to cotransfection. As with the two plasmid method, the method of FIGS. 12 and 13 is employed to rescue mutations in the fibre gene or in E4 or to rescue foreign DNA inserts as in FIG. 13.

To confirm that it is possible to insert into the adenovirus genome lox sites that flank a gene such as that encoding fibre, the plasmid shown in FIG. 14, called pAB14flox, was constructed. This plasmid contains a lox site inserted into the unique Blp I site in pAB14, which is located between the 3' terminus of the fibre gene and the coding regions of E4 genes. A second lox site was inserted into the XbaI site upstream of fibre. PAB14flox (fibre flanked by lox sites) was rescued into infectious virus by cotransfection with pFG 173 (described in Hanke, T., Graham, F. L., V. Lulitanond and D. C. Johnson, "Herpes simplex virus IgG Fc receptors induced using recombinant adenovirus vectors expressing glycoproteins E and I," Virology 177: 437–444,1990. PFG173 is available from Microbix Biosystems) as illustrated in FIG. 15, to produce Adfloxfibre. In two experiments, 293 cells were cotransfected with pAB14flox and pFG173, and two plaque isolates were obtained in each experiment (from 8 cotransfected dishes of 293 cells in experiment 1, and from 4 dishes in experiment 2). Two plaques were expanded and analysed and shown to have the expected DNA structure as illustrated in FIG. 15.

Upon transfection of 293Cre cells with DNA-TP complex of an Ad virus, such as Adfloxfibre-TP depicted in FIG. 15, said floxed fibre gene is excised by site-specific recombination between similarly oriented lox P sites, resulting in noninfectious viral DNA (as fibre is an essential component of the virion) as illustrated in FIG. 12. Cotransfection of said 293Cre cells with a plasmid containing a single lox P site upstream of fibre, such as pFG23dX1lox, optionally carrying a fibre or E4 gene mutation or insertion of foreign DNA, results in high-efficiency site-specific recombination between the plasmid and viral DNA and results in a virus whose fibre gene is derived from the plasmid as illustrated in FIG. 12 or FIG. 13. Therefore, it will be readily appreciated by one skilled in the art that mutations, deletions or other modifications engineered in and around the fibre gene of the plasmid, are rescued into the infectious virus genome. As an example, not meant to be limiting, the combination of plasmid, virus DNA and recombinase as illustrated in FIGS. 12 and 13 leads to high-efficiency substitution of wild-type fibre with modified fibre genes for production of mutant viruses whose virion capsids contain altered fibre.

As a further example of the utility of this approach, a foreign DNA segment is introduced into a plasmid, such as pFG23dX1lox, between the lox site and the coding sequences of fibre, such that said foreign DNA segment is rescued into virus by cotransfection of 293Cre cells with DNA prepared from Adlox2fibre (FIG. 13). As in the examples described previously for use of the two plasmid system, said foreign DNA segment could be a separate expression cassette or could be a fusion of peptide sequences such as a ligand to a cell surface receptor.

Table 5 provides results documenting the efficiency with which Cre mediated recombination can be used to generate infectious virus by cotransfection of 293Cre cells as illustrated in FIG. 9. It is apparent that the efficiency of rescue is comparable to that shown in Tables 1 and 2 and is several fold higher than the efficiency of homologous recombination (pFG173+pFG23dX1).

EXAMPLE 10

Use of Alternate Adenoviral Vector Systems According to this Invention

Those skilled in the art will recognize, based on the instant disclosure, that in the system described herein according to FIG. 8C, the left most lox site is not essential when the viral DNA is digested with enzymes such as those depicted, namely AsuII and/or SwaI. It will also be recognized that enhanced rescue of mutations or inserts into the viral genome by cotransfection of cells with a plasmid plus a viral DNA fragment with TP does not require a TP at both ends so the large viral DNA fragment generated by AsuII and/or SwaI digestion and having a TP at the right end only is sufficient for this system to operate efficiently. Similarly in the systems disclosed according to FIGS. 12 and 13, only the lox site 5' of fibre is necessary if the viral DNA-TP is cleaved with one or more enzymes that cut to the right, e.g. in fibre or in E4. If there are not naturally occurring restriction sites suitable for this purpose, such sites may easily be engineered by those of ordinary skill in the art, based on the present disclosure. For example we have identified a Blp I site between the 3' end of fibre and the coding sequences for E4 that can be used to insert a synthetic DNA. As illustrated in FIG. 14 we inserted a lox DNA sequence into this site but we could easily have introduced DNA containing a restriction endonuclease site that is not present elsewhere in the viral genome, and said restriction site could be rescued into an infectious virus as illustrated in FIG. 15.

It will further be recognized, based on the present disclosure, that the combination of Cre-lox with the two plasmid system will have widest application because of its simplicity: only readily prepared plasmid DNA is required, no restriction enzyme digestions are required, no possible background of parental viruses has to be contended with, and the system is more than adequately efficient for most purposes. Nonetheless, when enhanced levels of infectivity are required, utilization of the methods disclosed herein for use of viral DNA incorporating bound terminal protein may also benefit through combination with the site-specific recombination techniques taught herein.

---

What is claimed is:

1. A method for making an infectious adenovirus which comprises contacting a cell or introducing into a cell:
 (a) either (i) a first nucleic acid sequence encoding adenovirus sequences which, in the absence of intermolecular recombination, are insufficient to encode an infectious, replicable or packageable adenovirus, said first nucleic acid sequence comprising at least one site-specific recombinase recognition target site which is recognized by a site-specific recombinase or (ii) a first nucleic acid sequence encoding adenovirus sequences which are sufficient to encode an infectious, replicable or packageable adenovirus and comprising at least one site-specific recombinase recognition target site which is recognized by a site-specific recombinase, wherein contact of said first nucleic acid with said site-specific recombinase results in excision of sequences from said first nucleic acid sequence such that, in the absence of intermolecular recombination, said adenovirus of (ii) is rendered replication or packaging defective;
 (b) a second nucleic acid sequence encoding adenovirus sequences which, in the absence of adenoviral replication factors provided in trans or intermolecular recombination with said first nucleic acid sequence, are insufficient to encode an infectious, replicable or packageable adenovirus, said second nucleic acid sequence comprising at least one recombinase recognition target site sufficiently identical with said recombinase recognition target site in said first nucleic acid as to be recognized by the same site-specific recombinase which recognizes said site-specific recombinase recognition target site in said first nucleic acid;
whereby said first and said second nucleic acid sequences, in combination and following site-specific intermolecular recombination, result in production of an infectious adenovirus, wherein a site-specific recombinase which recognizes said site-specific recombinase recognition target sites is either (i) expressed by a cell into which said first and said second nucleic acids are introduced, (ii) operatively encoded by said first nucleic acid, said second nucleic acid or both, or (iii) is provided in trans through expression from a third nucleic acid or is provided in trans as an active protein, and with the proviso that an adenovirus encoded terminal protein is not linked to the first or to the said second nucleic acid sequence.

2. The method according to claim 1 wherein said second nucleic acid sequence is a plasmid comprising:
 (i) all or most of the left ITR and the packaging signal contained within the leftmost approximately 350 nt of the adenovirus genome;
 (ii) a polycloning site or a foreign DNA or an expression cassette; and
 (iii) a lox P site 3' of said polycloning site, foreign DNA, or an expression cassette.

3. The method according to claim 1 wherein said first nucleic acid sequence is a plasmid containing a circularized adenovirus DNA molecule encoding adenovirus sequences which, in the absence of intermolecular recombination, are insufficient to encode an infectious, replicable or packageable adenovirus.

4. The method according to claim 3 wherein said plasmid includes a bacterial origin of DNA replication and an antibiotic resistance gene for selection in bacteria.

5. The method according to claim 3 wherein said adenovirus PNA has a deletion of an adenoviral packaging signal, or wherein said packaging signal is flanked on either side by at least one of said site-specific recombinase recognition sites.

6. The method according to claim 5 wherein said adenovirus DNA comprises (i) a deletion of, (ii) a modification in, or (iii) a flanking with a site-specific recombinase recognition site of, an adenoviral gene selected from the group consisting of adenoviral E1 sequences extending beyond said packaging signal, adenoviral fibre gene sequences, adenoviral E3 gene sequences, adenoviral E4 gene sequences, and combinations thereof.

7. A recombinant adenovirus vector system comprising:
 (a) either (i) a first nucleic acid sequence encoding adenovirus sequences which, in the absence of intermolecular recombination, are insufficient to encode an infectious, replicable or packageable adenovirus, said first nucleic acid sequence comprising at least one site-specific recombinase recognition target site which is recognized by a site-specific recombinase or (ii) a first nucleic acid sequence encoding adenovirus sequences which are sufficient to encode an infectious, replicable or packageable adenovirus and comprising at least one site-specific recombinase recognition target site which is recognized by a site-specific recombinase, wherein contact of said first nucleic acid with said site-specific recombinase results in excision of sequences front said first nucleic acid sequence such that, in the absence of intermolecular recombination, said adenovirus of (ii) is rendered replication or packaging defective;
 (b) a second nucleic acid sequence encoding adenovirus sequences which, in the absence of adenoviral replication factors provided in trans or intermolecular recombination with said first nucleic acid sequence, are insufficient to encode an infectious, replicable or packageable adenovirus, said second nucleic acid sequence comprising at least one recombinase recognition target site sufficiently identical with said recombinase recognition target site in said first nucleic acid as to be recognized by the same site-specific recombinase which recognizes said site-specific recombinase recognition target site in said first nucleic acid;
whereby said first and said second nucleic acid sequences, in combination and following site-specific intermolecular recombination, result in production of an infectious adenovirus, wherein a site-specific recombinase which recognizes said site-specific recombinase recognition target sites is either (i) expressed by a cell into which said first and said second nucleic acids are introduced, (ii) operatively encoded by said first nucleic acid, said second nucleic acid or both, or (iii) is provided in trans through expression from a third nucleic acid or is provided in trans as an active protein, and with the proviso that an adenovirus encoded terminal protein is not linked to the first or to the said second nucleic acid sequence.

8. The recombinant adenovirus vector system of claim 7 wherein said cell further expresses adenoviral E1.

9. The recombinant adenovirus vector system of claim 7 wherein said first nucleic acid sequence and said second nucleic acid sequence are cotransfected into said cell to produce an infectious virus vector comprising a left end, a polycloning site, foreign DNA, or an expression cassette derived from said second nucleic acid sequence, joined to the remaining portion of the viral DNA derived from said first nucleic acid sequence.

10. The recombinant adenovirus vector system according to claim 7 wherein said first nucleic acid sequence comprises a recombinase recognition site and a deletion in the adenoviral fibre gene.

11. A kit for construction of a recombinant adenovirus vector comprising:
   (a) either (i) a first nucleic acid sequence encoding adenovirus sequences which, in the absence of intermolecular recombination, are insufficient to encode an infectious, replicable or packageable adenovirus, said first nucleic acid sequence comprising at least one site-specific recombinase recognition target site which is recognized by a site-specific recombinase or (ii) a first nucleic acid sequence encoding adenovirus sequences which are sufficient to encode an infectious, replicable or packageable adenovirus and comprising at least one site-specific recombinase recognition target site which is recognized by a site-specific recombinase, wherein contact of said first nucleic acid with said site-specific recombinase results in excision of sequences from said first nucleic acid sequence such that, in the absence of intermolecular recombination, said adenovirus of (ii) is rendered replication or packaging defective;
   (b) a second nucleic acid sequence encoding adenovirus sequences which, in the absence of adenoviral replication factors provided in trans or intermolecular recombination with said first nucleic acid sequence, are insufficient to encode an infectious, replicable or packageable adenovirus, said second nucleic acid sequence comprising at least one recombinase recognition target site sufficiently identical with said recombinase recognition target site in said first nucleic acid as to be recognized by the same site-specific recombinase which recognizes said site-specific recombinase recognition target site in said first nucleic acid; and
   (c) a cell wherein, when said first nucleic acid sequence and said second nucleic acid sequence are cotransfected and recombined through the action of a recombinase which recognizes said recombinase recognition sites, said recombinant adenovirus vector, packaged and infectious, is constructed, with the proviso that an adenovirus encoded terminal protein is not linked to the first or to the said second nucleic acid sequence.

12. The kit according to claim 11 wherein said cell of (c) is selected from the group consisting of 293 cells expressing Cre, PER-C6 cells expressing Cre, and 911 cells expressing Cre, and wherein said recombinase recognition sites are lox sites.

13. A recombinant adenovirus vector system comprising:
   (a) either (i) a first nucleic acid sequence encoding adenovirus sequences which, in the absence of intermolecular recombination, are insufficient to encode an infectious, replicable or packageable adenovirus, said first nucleic acid sequence comprising at least one site-specific recombinase recognition target site which is recognized by a site-specific recombinase or (ii) a first nucleic acid sequence encoding adenovirus sequences which are sufficient to encode an infectious, replicable or packageable adenovirus, said first nucleic acid sequence comprising (A) at least one restriction enzyme recognition site such that upon restriction of said nucleic acid with a restriction enzyme which recognizes said site, a site-specific recombinase recognition target site remains intact, but said adenovirus of (ii) is rendered replication or packaging deficient, or (B) wherein said nucleic acid comprises at least one site-specific recombinase recognition site which is recognized by a site-specific recombinase, wherein contact of said first nucleic acid with said site-specific recombinase results in excision of sequences from said first nucleic acid sequence such that, in the absence of intermolecular recombination, said adenovirus of (ii) is rendered replication or packaging defective;
   (b) a second nucleic acid sequence encoding adenovirus sequences which, in the absence of adenoviral replication factors provided in trans or intermolecular recombination with said first nucleic acid sequence, are insufficient to encode an infectious, replicable or packageable adenovirus, said second nucleic acid sequence comprising at least one recombinase recognition target site sufficiently identical with said recombinase recognition target site in said first nucleic acid as to be recognized by the same site-specific recombinase which recognizes said site-specific recombinase recognition target site in said first nucleic acid;
with the proviso that an adenovirus encoded terminal protein is not linked to the first or to the said second nucleic acid sequence, wherein said first and said second nucleic acid sequences, in combination and following site-specific intermolecular recombination, result in production of an infectious adenovirus, and wherein a site-specific recombinase which recognizes said site-specific recombinase recognition target sites is either (i) expressed by a cell into which said first and said second nucleic acids are introduced, (ii) operatively encoded by said first nucleic acid, said second nucleic acid or both, or (iii) is provided in trans through expression from a third nucleic acid or is provided in trans as an active protein.

14. The method according to claim 1 wherein said at least one site-specific recombinase recognition target site of said first nucleic acid sequence and said at least one site-specific recombinase recognition target site of said second nucleic acid sequence each is comprised of a loxP sequence, and wherein said site-specific recombinase is comprised of Cre.

15. The method according to claim 1 wherein said at least one site-specific recombinase recognition target site of said first nucleic acid sequence and said at least one site-specific recombinase recognition target site of said second nucleic acid sequence each is comprised of an frt sequence, and wherein said site-specific recombinase is comprised of FLP.

16. The recombinant adenovirus vector system according to claim 7 wherein said at least one site-specific recombinase recognition target site of said first nucleic acid sequence and said at least one site-specific recombinase recognition target site of said second nucleic acid sequence each is comprised of a loxP sequence, and wherein said site-specific recombinase is comprised of Cre.

17. The recombinant adenovirus vector system according to claim 7 wherein said at least one site-specific recombinase recognition target site of said first nucleic acid sequence and said at least one site-specific recombinase recognition target site of said second nucleic acid sequence each is comprised of an frt sequence, and wherein said site-specific recombinase is comprised of FLP.

18. The kit according to claim 11 wherein said at least one site-specific recombinase recognition target site of said first nucleic acid sequence and said at least one site-specific recombinase recognition target site of said second nucleic acid sequence each is comprised of a loxP sequence, and wherein said site-specific recombinase is comprised of Cre.

19. The kit according to claim 11 wherein said at least one site-specific recombinase recognition target site of said first nucleic acid sequence and said at least one site-specific recombinase recognition larger site of said second nucleic acid sequence each is comprised of an frt sequence, and wherein said site-specific recombinase is comprised of FLP.

20. The recombinant adenovirus vector system according to claim 7 wherein said at least one site-specific recombinase recognition target site of said first nucleic acid sequence and said at least one site-specific recombinase recognition target site of said second nucleic acid sequence each is comprised of a loxP sequence, and wherein said site-specific recombinase is comprised of Cre.

21. The recombinant adenovirus vector system according to claim 7 wherein said ax least one site-specific recombinase recognition target site of said first nucleic acid sequence and said at least one site-specific recombinase recognition target site of said second nucleic acid sequence each is comprised of an frt sequence, and wherein said site-specific recombinase is comprised of FLP.

* * * * *